United States Patent
Zeldis

(10) Patent No.: US 7,148,252 B2
(45) Date of Patent: Dec. 12, 2006

(54) USE OF BENZOPYRANONES FOR TREATING OR PREVENTING A PRIMARY BRAIN CANCER OR A BRAIN METASTASIS

(75) Inventor: Jerome B. Zeldis, Princeton, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 289 days.

(21) Appl. No.: 10/261,198

(22) Filed: Sep. 30, 2002

(65) Prior Publication Data
US 2003/0149025 A1   Aug. 7, 2003

Related U.S. Application Data

(60) Provisional application No. 60/327,060, filed on Oct. 3, 2001.

(51) Int. Cl.
  *A61K 31/35*   (2006.01)
  *A61P 35/04*   (2006.01)
(52) U.S. Cl. .............. 514/456; 514/233.5; 514/457
(58) Field of Classification Search ............ 514/233.5, 514/452, 456
  See application file for complete search history.

(56) References Cited

U.S. PATENT DOCUMENTS

| | | | |
|---|---|---|---|
| 6,291,456 B1 | 9/2001 | Stein et al. | |
| 6,331,562 B1 | 12/2001 | Bhagwat et al. | |
| 6,372,739 B1 * | 4/2002 | Stein et al. | 514/233.5 |

OTHER PUBLICATIONS

Al-Saffar et al., 1996, "Assessment of the role of GM-CSF in the cellular transformation and the development of erosive lesions around orthopaedic implants", Am J Clin Pathol. 105(5):628-39.
Alonzi et al., 1998, "Interleukin 6 is required for the development of collagen-induced arthritis", J Exp Med. 187(4):461-8.
Barkhem et al., 1998, "Differential response of estrogen receptor alpha and estrogen receptor beta to partial estrogen agonists/antagonists", Mol Pharmacol. 54(1):105-12.
Blsmar et al., 1995, "Increased cytokine secretion by human bone marrow cells after memopause or discontinuation of estrogen replacement", J Clin Endocrinol Metab. 80(11):3351-5.
Bodine et al., 1998, "Estrogen receptor-alpha is developmentally regulated during osteoblast differentiation and contributes to selective responsiveness of gene expression", Endocrinology. 139(4):2048-57.
Brandenberger et al., 1998, "Estrogen receptor alpha (ER-alpha) and beta (ER-beta) mRNAs in normal ovary, ovarian serous cystadenocarcinoma and ovarian cancer cell lines: down-regulation of ER-beta in neoplastic tissues", J Clin Endocrinol Metab. 83(3):1025-8.
Chen et al., 2001, "Molecular basis for the constitutive activity of estrogen-related receptor alpha-1", J Biol Chem. 276(30):28465-70.
Chung et al., 2002, "Resistance to tamoxifen-induced apoptosis is associated with direct interaction between Her2/neu and cell membrane estrogen receptor in breast cancer", Int J Cancer. 97(3):306-12.
Clinton and Hua, 1997, "Estrogen action in human ovarian cancer", Crit Rev Oncol Hematol. 25(1):1-9.
Cooke et al., 1998, "Mechanism of estrogen action: lessons from the estrogen receptor-alpha knockout mouse", Biol Reprod. 59(3):470-5.
Couse et al., 1997, "Tissue distribution and quantitative analysis of estrogen receptor-alpha (ERalpha) and estrogen receptor-beta (ERbeta) messenger ribonucleic acid in the wild-type and ERalpha-knockout mouse", Endocrinology. 138(11):4613-21.
Coward et al., 2001, "4-Hydroxytamoxifen binds to and deactivates the estrogen-related receptor gamma", Proc Natl Acad Sci U S A. 98(15):8880-4.
Das et al., 1997, "Estrogenic responses In estrogen receptor-α deficient mice reveal a distict estrogen signaling pathway", Proc. Natl. Acad. Sci. USA 94:12786-91.
Devlin et al., 1998, "IL-6 mediates the effects of IL-1 or TNF, but not PTHrP or 1,25(OH)2D3, on osteoclast-like cell formation in normal human bone marrow cultures", J Bone Miner Res. Mar. 1998;13(3):393-9.
Duan et al., 1998, "Estrogen-induced c-fos protooncogene expression in MCF-7 human breast cancer cells: role of estrogen receptor Sp1 complex formation", Endocrinology. 139(4):1981-90.
Enmark et al., 1997, "Human estrogen receptor beta-gene structure, chromosomal localization, and expression pattern", J. Clin Endocrinol Metab. 82(12):4258-65.
Eustace et al., 1993, "Interleukin-6 (IL-6) functions as an autocrine growth factor in cervical carcinomas in vitro", Gynecol Oncol. 50(1):15-19.
Farhat et al., 1996, "The vascular protective effects of estrogen", FASEB J. 10(5):615-24.
Garrett et al., 1997, "A murine model of human myeloma bone disease", Bone 20(6):515-20.

(Continued)

Primary Examiner—Christopher S. F. Low
Assistant Examiner—C. Delacroix-Muirheid
(74) Attorney, Agent, or Firm—Jones Day

(57) ABSTRACT

This invention relates to methods for using benzopyranones, or their pharmaceutically acceptable salts, for treating or preventing a primary brain cancer or a brain metastasis. The benzopyranones have the formula:

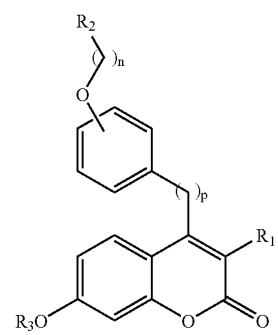

wherein $R_1$, $R_2$, $R_3$, n and p are as defined herein.

78 Claims, No Drawings

OTHER PUBLICATIONS

Girasole et al., 1992, "17 beta-estradiol inhibits interleukin-6 production by bone marrow-derived stromal cells and osteoblasts in vitro: a potential mechanism for the antiosteoporotic effect of estrogens", J Clin Invest. 89(3):883-91.

Grese et al., 1997, "Structure-activity relationships of selective estrogen receptor modulators: modifications to the 2-arylbenzothiophene core of raloxifene", J Med Chem. 40(2):146-67.

Gupta et al., 1985, "7-hydroxy-4-phenyl-3(4-hydroxyphenyl)-coumarin—a new interceptive agent", Indian J Exp Biol. 23(11):638-40.

Gustafsson et al., 1998, "Therapeutic potential of selective estrogen receptor modulators", Curr Opin Biol. 2(4):508-11.

Hata et al., 1998, "Role of estrogen and estrogen-related growth factor in the mechanism of hormone dependency of endometrial carcinoma cells", Oncology. 55 Suppl 1:35-44.

Hughes et al., 1996, "Estrogen promotes apoptosis of murine osteoclasts mediated by TGF-beta", Nat Med. 2(10):1132-6.

Iafrati et al., 1997, "Estrogen inhibits the vascular injury response in estrogen receptor alpha-deficient mice", Nat Med. 3(5):545-8.

Jansson et al., 1994, "Estrogen induces a potent suppression of experimental autoimmune encephalomyelitis and collagen-induced arthritis in mice", J Neuroimmunol. 53(2):203-7.

Jeltsch et al., 1987, "Structure of the human oestrogen-responsive gene pS2", Nucleic Acids Res. 15(4):1401-14.

Jilka et al, 1995, "Estrogen loss upregulates hematopoiesis in the mouse: a mediating role of IL-6", Exp Hematol. 23(6):500-6.

Jilka et al., 1992, "Increased osteoclast development after estrogen loss: mediation by interleukin-6", Science 57(5066):88-91.

Kelly et al., 1999, "Estrogen Modulation of G-protein-coupled Receptors", Trends Endocrinol Metab. 10(9):369-374.

Kimble et al., 1996, "Estrogen deficiency increases the ability of stromal cell to support murine osteoclastogenesis via an interleukin-1and tumor necrosisfactor-mediatedstimulation of macrophage colony-stimulating factor production", J Biol Chem. 271(46):28890-7.

Kimble et al., 1995, "Simultaneous block of interkeukin-1 and tumor necrosis factor is required to completely prevent bone loss in the early postovariectomy period", Endocrinology. 136(7):3054-61.

Klein et al., 1991, "Murine anti-interleukin-6 monoclonal antibody therapy for a patient with plasma cell leukemia", Blood. 78(5):1198-204.

Klein et al., 1989, "Paracrine rather than autocrine regulation of myeloma-cell growth and differentiation by Interleukin-6", Blood. 73(2):517-26.

Koo et al., 1992, "Interkeukin-6 and renal cell cancer: production, regulation, and growth effects", Cancer Immunol Immunother. 35(2):97-105.

Korach et al., 1994, "Insights from the study of animals lacking functional estrogen receptor", Science 266(5190):1524-7.

Krege et al., 1998, "Generation and reproductive phenotypes of mice lacking estrogen receptor beta", Proc Natl Acad Sci U S A.95(26):15677-82.

Kuiper et al., 1997, "Comparison of the ligand binding specificity and transcript tissue distribution of estrogen receptors alpha and beta", Endocrinology. Mar. 1997;138(3):863-70.

Kurihara et al., 1989, "Generation of osteoclasts from isolated hematopoietic progenitor cells", Blood 74(4):1295-302.

Laflamme et al., 1998, "Expression and neuropeptidergic characterization of estrogen receptors (ERalpha and ERbeta) throughout that rat brain: anatomical evidence of distinct roles of each subtype", J Neurobiol. 36(3):357-78.

Lednicer et al., 1965, "Mammalian Antifertility Agents: Basic Ethers of 3,4—Diphenylcoumarin", J. Med. Chem. 8:725-726.

Leisten Interleukin-6 serum levels correlate with footpad swelling in adjuvant-induced arthritic Lewis rats treated with cyclosporin A or indomethacin. Clin Immunol Immunopathol. Jul. 1990;56(1):108-15.

Levin et al., 1999, "Cellular Functions of the Plasma Membrane Estrogen Receptor", Trends Endocrinol Metab. 10(9):374-377.

Lorenzo et al., 1987, "Colony-stimulating factors regulate the development of multinucleated osteoclasts from recently replicated cells in vitro", J Clin Invest. 80(1):160-4.

Lu et al., 2001, "Transcriptional regulation of the estrogen-inducible pS2 breast cancer marker gene by the ERR family of orphan nuclear receptors", Cancer Res. 15;61(18):6755-61.

MacDonald et al., 1986, "Effects of human recombinant CSF-GM and highly purified CSF-1 on the formation of multinucleated cells with osteoclast characteristics in long-term bone marrow cultures", J Bone Miner Res. 1(2):227-33.

Martinez-Maza et al., 1992, "IL6 and AIDS", Res Immunol. 143(7):764-9.

Micheli et al., 1962, "Coumestrol, Plant Phenolics, and Synthetic Estrogens: a Correlation of Structure and Activity", 321-335.

Nadal et al., 2001, "The plasma membrane estrogen receptor: nuclear or unclear?", Trends Pharmacol Sci. 22(12):597-9.

Ogawa et al., 1997, "Behavioral effects of estrogen receptor gene disruption in male mice", Proc Natl Acad Sci U S A. 94(4):1476-81.

Ohshima et al., 1998, "Interleukin 6 plays a key role in the development of antigen-induced arthritis", Proc. Natl Acad Sci U S A. 95(14):8222-6.

Okamoto et al., 1997, "Interleukin-6 as a paracrine and autocrine growth factor in human prostatic carcinoma cells in vitro", Cancer Res. 57(1):141-6.

Okamoto et al., 1997, "Autocrine effect of androgen on proliferation of an androgen responsive prostatic carcinoma cell line, LNCAP: role of interleukin-6", Endocrinology. 138(11):5071-4.

Pacifici 1996, "Estrogen, cytokines, and pathogenesis of postmenopausal osteoporosis", J Bone Miner Res. 11(8):1043-51.

Paech et al., 1997, "Differential ligand activation of estrogen receptors ERalpha and ERbeta at AP1 sites", Science. 277(5331):1508-10.

Parfitt et al., 1996, "A new model for the regulation of bone resorption, with paticular reference to the effects of bisphosphonates", J Bone Miner Res. 11(2):150-9.

Passeri et al., 1993, "Increased Interleukin-6 production by murine bone marrow and bone cells after estrogen withdrawal", Endocrinology. 133(2):822-8.

Poll et al., 1994, "Interleukin-6 deficient mice are protected from bone loss caused by estrogen depletion", EMBO J. 13(5):1189-96.

Pollard et al., 1968, "The oestrogenic and anti-oestrogenic activity of some synthetic steroids and non-steroids", Steroids.

Ray et al., 1987, "Enhanced antifertility activity of non-steroidal molecules with 3-n-butylamino-2-hydroxypropyloxy side chain", Contraception.35(3):283-7.

Reddy et al., 1994, "Interleukin-6 antisense deoxyoligonucleotides inhibit bone resorption by giant cells from human giant cell tumors of bone", J Bone Miner Res. 9(5):753-7.

Rissman et al., 1997, "Estrogen receptors are essential for female sexual receptivity", Endocrinology 138(1):507-10.

Rissman et al., 1997, "Estrogen receptor function as revealed by knockout studies: neuroendocrine and behavioralaspects", Horm Behav. 31(3):232-43.

Rohiff et al., 1998, "Prostate cancer cell growth inhibition by tamoxifen is associated with inhibition of protein kinase C and induction of p21(waf1/cip1)", Prostate. 37(1):51-9.

Sar et al., 1999, "Differential expression of estrogen receptor-beta and estrogen receptor-alpha in the rat ovary", Endocrinology. 140(2):963-71.

Schiller et al., 1997, "17Beta-estradiol antagonizes effects of 1alpha,25-dihydroxyvitamin D3 on interleukin-6 production and osteoclast-like cell formation in mouse bone marrow primary cultures", Endocrinology 138(11):4567-71.

Shinar et al., 1990, "The effect of hemopoletic growth factors on the generation of osteoclast-like cells in mouse bone marrow cultures", Endocrinology 126(3):1728-35.

Shughrue et al., 1997, "Responses in the brain of estrogen receptor alpha-disrupted mice", Proc Natl Acad Sci USA ,94(20):11008-12.

Shughrue et al., 1997, "The distribution of estrogen receptor-beta mRNA in forebrain regions of the estrogen receptor-alpha knockout mouse", Endocrinology. 138(12):5649-52.

Shughrue et al., 1997, "Comparative distribution of estrogen receptor-alpha and -beta mRNA in the rat central nervous system", J Comp Neurol. 388(4):507-25.

Siegall et al., 1990, "Expression of the interleukin 6 receptor and interleukin 6 in prostate carcinoma cells", Cancer Res. 50(24):7786-8.

Simpson et al., 1998, "Estrogen regulation of transforming growth factor-alpha in ovarian cancer", J Steroid Biochem Mol Biol. 64(3-4):137-45.

Stein et al., 1995, "Repression of the interleukin-6 promoter by estrogen receptor is mediated by NF-kappa B and C/EBP beta", Mol Cell Biol. 15(9):4971-9.

Suzuki et al., 1996, "Caicitonin-induced changes in the cytoskeleton are mediated by a signal pathway associated with protein kinase A in osteoclasts", Endocrinology. 137(11):4685-90.

Tartour et al., 1994, "Analysis of interleukin 6 gene expression in cervical neoplasia using a quantitative polymerase chain reaction assay: evidence for enhanced interleukin 6 gene expression in invasive carcinoma", Cancer Res. 54(23):6243-8.

Tremblay et al., 2001, 4-Hydroxytamoxifen is an isoform-specific inhibitor of orphan estrogen-receptor-related (ERR) nuclear receptors beta and gamma. Endocrinology 142(10):4572-5.

Tremblay et al., "EM-800, a novel antiestrogen, acts as a pure antagonist of the transcriptional functions of estrogen receptors alpha and beta", Endocrinology 139(1):111-8, (1998).

Tsukamoto et al., 1992, "Interleukin-6 in renal cell carcinoma", J. Urol. 148(6):1778-81: discussion 1781-2.

Turner et al., 1998, "Differential responses of estrogen target tissues in rats including bone to clomiphene, enclomiphene, and zuclomiphene", Endocrinology. 139(9):3712-20.

Verma et al., 1993, "Microwave induced alteration in the neuron specific enolase gene expression", Indian J. Chem. 32B:239-243.

Weissglas et al., 1997, "The role of interleukin-6 in the induction of hypercalcemia in renal cell carcinoma transplanted into nude mice", Endocrinology 138(5):1879-85.

Wendling et al., 1993, "Treatment of severe rheumatoid arthritis by anti-interleukin 6 monoclonal antibody", J Rheumatol 20(2):259-62.

Wyckoff et al., 2001, "Plasma membrane estrogen receptors are coupled to endothelial nitric-oxide synthase through Galpha(i)", J Biol Chem. 276(29):27071-6.

Yamashita et al., 1998, "Endocrine therapy in pancreatic carcinoma", Oncology. 55 Suppl 1:17-22.

Zhang et al., 1989, "Interleukin-6 is a potent myeloma-cell growth factor in patients with aggressive multiple myeloma", Blood. 74(1):11-3.

Cohen et al., 1976, "Acute Nonlymphocytic Leukemia Associated with Nitrosourea Chemotherapy: Report of Two Cases", Cancer Treat Rep. 60:1257-61.

Couldwell et al., 1996, "Treatment of Recurrent Mallgnant Gilomoas with Chronic Oral High Dose Tamoxifen", Clin. Cancer Res. 2:619-622.

Neubauer et al., 1995, "Raloxifene (LY156758) Produces Antimetastatic Responses and Extends Survival in the PAIII Rat Prostatic Adenocarcinoma Model", Prostate 27:220-9.

Hui et al., 2004, "Agents with Selective Estrogen Receptor (ER) Modulator Activity Induce Apoptosis *In vitro* and *In vivo* in ER-Negative Glioma Cells", Cancer Research 64:9115-9123.

* cited by examiner

USE OF BENZOPYRANONES FOR TREATING OR PREVENTING A PRIMARY BRAIN CANCER OR A BRAIN METASTASIS

This application claims the benefit of U.S. Provisional Application No. 60/327,060, filed Oct. 3, 2001, the disclosure of which is incorporated by reference herein in its entirety.

1. FIELD OF THE INVENTION

This invention relates to methods for using benzopyranones, or their pharmaceutically acceptable salts, for treating or preventing a primary brain cancer or a brain metastasis.

2. BACKGROUND OF THE INVENTION

There are about 10,000 incidences of brain tumors each year, and about 4000 incidences of spinal cord tumors each year (Kornblith et al.(1985), *Cancer: Principles and Practice of Oncology*, $2^{nd}$ Ed., DeVita, V., Hellman, S., Rosenberg, S., eds., J. B. Lippincott Company, Philadelphia, Chapter 41: Neoplasms of the Central Nervous System). Central nervous system (CNS) tumors comprise the most common group of solid tumors in young patients (Id). Gliomas comprise about 60% of all primary CNS tumors, with the most common cerebral primary tumors being astrocytomas, meningioma, oligodendroglioma and histocytic lymphoma (Id). Gliomas usually occur in the cerebral hemispheres of the brain, but may be found in other areas such as the optic nerve, brain stem or cerebellum (Brain Tumor Society; www/tbts.org/primary.htm).

Gliomas are classified into groups according to the type of glial cell from which they originate (Id). The most common types of glioma are astrocytomas. These tumors develop from star-shaped glial cells called astrocytes. Astrocytomas are assigned to grades according to their malignancy. Low-grade astrocytomas, also known as grade I and II astrocytomas, are the least malignant, grow relatively slow and can often be completely removed using surgery. Mid-grade astrocytomas, also known as grade III astrocytomas, grow more rapidly and are more malignant. Grade III astrocytomas are treated with surgery followed by radiation and some chemotherapy. High-grade astrocytomas, also known as grade IV astrocytomas, grow rapidly, invade nearby tissue, and are very malignant. Grade IV astrocytomas are usually treated with surgery followed by a combination of radiation therapy and chemotherapy. Glioblastoma multiforme are grade IV astrocytomas, which are among the most malignant and deadly primary brain tumors (Id).

Traditionally, treatment of astrocytomas has involved surgery to remove the tumor, followed by radiation therapy. Chemotherapy may also be administered either before or after radiation therapy (Kornblith et al.(1985), *Cancer: Principles and Practice of Oncology*, $2^{nd}$ Ed., DeVita, V., Hellman, S., Rosenberg, S., eds., J. B. Lippincott Company, Philadelphia, Chapter 41: Neoplasms of the Central Nervous System). While the same surgical techniques and principles have applied to treating glioblastoma multiforme and less malignant brain tumors, total removal of a glioblastoma multiforme tumor has been more difficult to achieve (Id).

The prognosis for a patient diagnosed as having a grade IV astrocytoma brain tumor has traditionally been poor. While a person treated for a grade I astrocytoma can commonly survive 10 years or more without recurrence, the mean length of survival for a patient with a grade IV astrocytoma tumor is 15 weeks after surgical treatment. Because of the high malignant-growth potential of grade IV astrocytoma tumors, only 5% of patients have survived for 1 year following surgical treatment alone, with a near 0% survival rate after 2 years. Radiation treatment in combination with surgical treatment increases the survival rate to about 10% after 2 years of treatment; however, virtually no patients survive longer than 5 years (Id).

Nitrosourea chemotherapeutic agents have normally been used in the treatment of brain tumors. The key property of these compounds is their ability to cross the blood-brain barrier. 1-3-bis-2-chloroethyl-1-nitrosourea (BCNU, also known as Carmustine) was the first of these to be used clinically. While the use of BCNU in combination with surgery and/or radiation treatment has been shown to be beneficial, it has not cured glioblastoma multiforme brain tumors. Additionally, complications with prolonged nitrosourea treatment have been reported (Cohen et al. (1976), *Cancer Treat. Rep.* 60, 1257–1261). These complications include pulmonary fibrosis, hepatic toxicity, renal failure and cases of secondary tumors associated with nitrosourea treatment.

The use of estrogen receptor modulators Tamoxifen and Raloxifene in cancer treatment has also been investigated. Tamoxifen has been used in human clinical trials involving the treatment of recurrent malignant glial tumors (Couldwell et al.(1996), *Clin. Cancer Res.* 2, 619–622). Raloxifene has been shown to inhibit metastasis of a tail tumor to the lungs in a rat model (Neubauer et al.(1995), *Prostate* 27, 220–229).

While a treatment regimen of surgery, radiation therapy and chemotherapy offers the opportunity for a modestly increased lifespan for patients with a grade IV astrocytoma brain tumor, the risks associated with each method of treatment are many. The benefits of treatment are minimal, and treatment can significantly decrease the quality of the patient's brief remaining lifespan. Accordingly, there remains a clear need in the art for primary brain cancer and brain metastasis prevention and treatment methods that overcome the disadvantages of the above-mentioned traditional approaches.

Citation or identification of any reference in section 2 of this application is not an admission that the reference is prior art to the present application.

3. SUMMARY OF THE INVENTION

The present invention relates to a method for treating or preventing a primary brain cancer or a brain metastasis in a patient, comprising administering to a patient in need thereof an effective amount of a compound of formula (I):

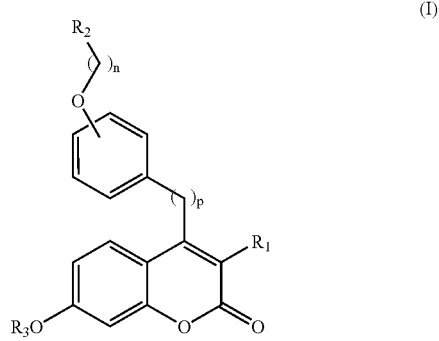

or a pharmaceutically acceptable salt thereof, wherein:
n is 0, 1, 2, 3 or 4;
p is 0, 1 or 2;
R$_1$ is an unsubstituted or substituted C$_{6-12}$aryl, C$_{7-12}$arylalkyl, C$_{3-12}$heterocycle or C$_{4-16}$heterocyclealkyl;
R$_2$ is NR$_a$R$_b$ wherein R$_a$ and R$_b$ are independently hydrogen, C$_{1-8}$alkyl, C$_{6-12}$aryl, or heterocycle, and wherein R$_a$ and R$_b$ are optionally substituted with up to three substituents independently selected from C$_{1-6}$alkyl, halogen, C$_{1-6}$alkoxy, hydroxy and carboxyl;
or R$_2$ is a heterocyclic ring of the following structure:

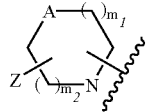

wherein
m$_1$ and m$_2$ are independently 0, 1 or 2, and both of m$_1$ and m$_2$ are not 0,
A is CH$_2$, O, S or NH,
Z represents 0, 1, 2 or 3 heterocyclic ring substituents selected from halogen, C$_{1-8}$alkyl, C$_{6-12}$aryl, C$_{7-12}$arylalkyl, C$_{3-12}$heterocycle, or C$_{4-16}$heterocyclealkyl,
and wherein any hydrogen atom on the heterocyclic ring may, taken together with a hydrogen atom on an adjacent atom of the heterocyclic ring, form a double bond;
R$_3$ is hydrogen, R$_4$, C(=O)R$_4$, C(=O)OR$_4$, CONHR$_4$, CONR$_4$R$_5$, or SO$_2$NR$_5$R$_5$;
R$_4$ and R$_5$ are independently C$_{1-8}$alkyl, C$_{6-12}$aryl, C$_{7-12}$arylalkyl, or a five- or six-membered heterocycle containing up to two heteroatoms selected from O, NR$_6$ and S(O)$_q$, wherein each of the above groups are optionally substituted with one to three substituents independently selected from R$_7$ and q is 0, 1 or 2;
R$_6$ is hydrogen or C$_{1-4}$alkyl; and
R$_7$ is hydrogen, halogen, hydroxy, C$_{1-6}$alkyl, C$_{1-4}$alkoxy, C$_{1-4}$acyloxy, C$_{1-4}$thio, C$_{1-4}$alkylsulfinyl, C$_{1-4}$alkylsulfonyl, (hydroxy)C$_{1-4}$alkyl, C$_{6-12}$aryl, C$_{7-12}$aralkyl, COOH, CN, CONHR$_8$, SO$_2$NHR$_8$, NH$_2$, C$_{1-4}$alkylamino, C$_{1-4}$dialkylamino, NHSO$_2$R$_8$, NO$_2$, or a five- or six-membered heterocycle, where each occurrence of R$_8$ is independently C$_{1-6}$alkyl.

In certain embodiments, the cancers or metastasis to be treated or prevented in the present invention include, but are not limited to, primary intracranial central nervous system tumors. Primary intracranial central nervous system tumors include glioblastoma multiform; malignant astrocytomas; oligodendroglioma; ependymoma; low-grade astrocytomas; meningioma; mesenchymal tumors; pituitary tumors; nerve sheath tumors such as schwannomas; central nervous system lymphoma; medulloblastoma; primitive neuroectodermal tumors; neuron and neuron/glial tumors; craniopharyngioma; germ cell tumors; and choroid plexus tumors.

In other embodiments, the cancers or metastasis to be treated or prevented in the present invention include, but are not limited to, primary spinal tumors such as schwannoma, meningioma, ependymoma, sarcomas, astrocytoma, gliomas, vascular tumors, chordomas and epidermoids.

In other embodiments, the cancers or metastasis to be treated or prevented in the present invention include, but are not limited to, primary tumors responsible for brain metastasis such as lung (both small cell and non-small cell), breast, unknown primary, melanoma and colon.

3.1 Definitions

As used herein, a "C$_{6-12}$aryl" is an aromatic moiety containing from 6 to 12 carbon atoms. In one embodiment, the C$_{6-12}$aryl is selected from (but not limited to) phenyl, tetralinyl, and napthalenyl.

A "C$_{7-12}$aralkyl" is an arene containing from 7 to 12 carbon atoms, and has both aliphatic and aromatic units. In one embodiment, the C$_{7-12}$aralkyl is selected from (but not limited to) benzyl, ethylbenzyl (i.e., —(CH$_2$)$_2$phenyl), propylbenzyl and isobutylbenzyl.

A "C$_{3-12}$heterocycle" is a compound that contains a ring made up of more than one kind of atom, and which contains 3 to 12 carbon atoms, including (but not limited to) pyrrolyl, furanyl, thienyl, imidazolyl, oxazolyl, thiazolyl, pyrazolyl, pyrrolidinyl, pyridinyl, pyrimidinyl and purinyl.

A "C$_{4-16}$heterocyclealkyl" is a compound that contains a C$_{3-12}$heterocycle linked to a C$_{1-8}$alkyl.

A "C$_{1-8}$alkyl" is a straight chain or branched carbon chain containing from 1 to 8 carbon atoms, including (but not limited to) methyl, ethyl, and n-propyl. Similarly, a "C$_{1-x}$ alkyl has the same meaning, but wherein "x" represents the number of carbon atoms less than eight, such as C$_{1-6}$alkyl.

A "substituted" C$_{1-x}$ alkyl, C$_{6-12}$aryl, C$_{7-12}$aralkyl, C$_{3-12}$heterocycle, or C$_{4-16}$heterocyclealkyl moiety is a C$_{1-x}$ alkyl, C$_{6-12}$aryl, C$_{7-12}$aralkyl, C$_{3-12}$heterocycle, or C$_{4-16}$heterocyclealkyl moiety having at least one hydrogen atom replaced with a substituent.

A "substituent" is a moiety selected from halogen, —OH, —R', —OR', —COOH, —COOR', —COR', —CONH$_2$, —NH$_2$, —NHR', —NR'R', —SH, —SR', —SOOR', —SOOH and —SOR', where each occurrence of R' is independently selected from an unsubstituted or substituted C$_{1-8}$alkyl, C$_{6-12}$aryl, C$_{7-12}$aralkyl, C$_{3-12}$heterocycle or C$_{4-16}$heterocyclealky A "halogen" is fluoro, chloro, bromo or iodo.

The present invention can be understood more fully by reference to the following figures, detailed description and illustration examples, which are intended to exemplify non-limiting embodiments of the invention.

4. DETAILED DESCRIPTION OF THE INVENTION

As mentioned above, the present invention relates to methods for treating or preventing a primary brain cancer or a brain metastasis in a patient, comprising administering to a patient in need thereof an effective amount of a compound of formula (I):

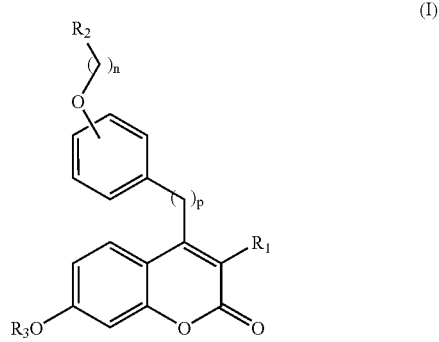

or a pharmaceutically acceptable salt thereof, wherein:
n is 0, 1, 2, 3 or 4;
p is 0, 1 or 2;
$R_1$ is an unsubstituted or substituted $C_{6-12}$aryl, $C_{7-12}$arylalkyl, $C_{3-12}$heterocycle or $C_{4-16}$heterocyclealkyl;
$R_2$ is $NR_aR_b$ wherein $R_a$ and $R_b$ are independently hydrogen, $C_{1-8}$alkyl, $C_{6-12}$aryl, or heterocycle, and wherein $R_a$ and $R_b$ are optionally substituted with up to three substituents independently selected from $C_{1-6}$alkyl, halogen, $C_{1-6}$alkoxy, hydroxy and carboxyl;
or $R_2$ is a heterocyclic ring of the following structure:

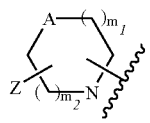

wherein
$m_1$ and $m_2$ are independently 0, 1 or 2, and both of $m_1$ and $m_2$ are not 0,
A is $CH_2$, O, S or NH;
Z represents 0, 1, 2 or 3 heterocyclic ring substituents selected from halogen, $C_{1-8}$alkyl, $C_{6-12}$aryl, $C_{7-12}$arylalkyl, $C_{3-12}$heterocycle, or $C_{4-16}$heterocyclealkyl,
and wherein any hydrogen atom on the heterocyclic ring may, taken together with a hydrogen atom on an adjacent atom of the heterocyclic ring, form a double bond;
$R_3$ is hydrogen, $R_4$, $C(=O)R_4$, $C(=O)OR_4$, $CONHR_4$, $CONR_4R_5$, or $SO_2NR_5R_5$;
$R_4$ and $R_5$ are independently $C_{1-8}$alkyl, $C_{6-12}$aryl, $C_{7-12}$arylalkyl, or a five- or six-membered heterocycle containing up to two heteroatoms selected from O, $NR_6$ and $S(O)_q$, wherein each of the above groups are optionally substituted with one to three substituents independently selected from $R_7$ and q is 0, 1 or 2;
$R_6$ is hydrogen or $C_{1-4}$ alkyl; and
$R_7$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $CONHOR_8$, $SO_2NHR_8$, $NH_2$, $C_{1-4}$alkylamino, $C_{1-4}$dialkylamino, $NHSO_2R_8$, $NO_2$, or a five- or six-membered heterocycle, where each occurrence of $R_8$ is independently $C_{1-6}$alkyl.

In one embodiment of the invention, the compounds useful for treating or preventing a primary brain cancer or a brain metastasis are those wherein p=0.

In another embodiment of the invention, the compounds useful for treating or preventing a primary brain cancer or a brain metastasis are those wherein p=1 or 2, preferably 1.

In another embodiment of this invention, the compounds useful for treating or preventing a primary brain cancer or a brain metastasis are those wherein A of the heterocyclic ring $R_2$ is $CH_2$; m is 1; and $m_2$ is 0 or 1, as represented by the following structures (i) and (ii), respectively:

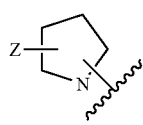

(i)

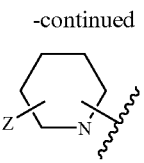

(ii)

In structures (i) and (ii) above, it should be noted that the hydrogen atoms are not depicted in order to clarify that the optional Z substituent(s) can be attached to any atom of the heterocyclic ring, and that the point of attachment to structure (I) can be through a carbon or nitrogen atom.

Thus, in more specific embodiments of the invention, the compounds useful for treating or preventing a primary brain cancer or a brain metastasis contain structures (i) and (ii) and, wherein Z is present, $R_2$ includes the following structures (iii) through (vi):

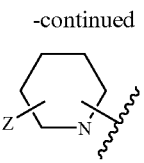

(iii)

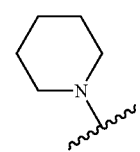

(iv)

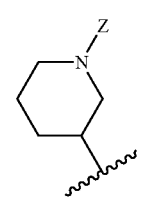

(v)

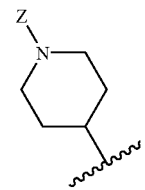

(vi)

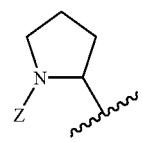

wherein Z is, for example, hydrogen or an alkyl group such as methyl.

In another embodiment of the invention, the compounds useful for treating or preventing a primary brain cancer or a brain metastasis are those wherein A of the heterocyclic ring $R_2$ is O or NH, $m_1$ is 1, and $m_2$ is 0 or 1, as represented by, for example, the following structures (vii) and (viii):

(vii)

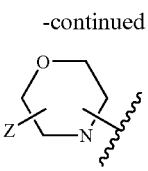

As with structures (i) and (ii) above, in structures (vii) and (viii) the hydrogen atoms are not depicted in order to clarify that the optional Z substituent(s) may be attached to any atom of the heterocyclic ring, and that the point of attachment to structure (I) may be through a carbon or nitrogen atom.

In addition to the above-depicted structures, any hydrogen atom of the heterocyclic ring may be taken together with a hydrogen atom attached to an adjacent heterocyclic ring atom to form a double bond. For example, with regard to structure (vii) above, corresponding unsaturated analogs include the following structures (ix), (x) and (xi):

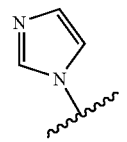

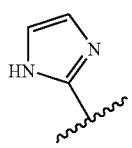

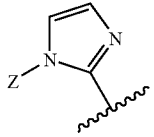

In one embodiment of this invention, $R_1$ is an unsubstituted or substituted phenyl, and the compounds useful in the methods of this invention have the following structure (II):

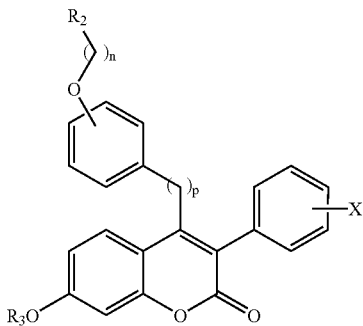

wherein X represents one or more optional substitutents as defined above, and $R_2$, $R_3$, n and p are as defined above.

In another embodiment, the compounds useful for treating or preventing a primary brain cancer or a brain metastasis are those wherein $R_3$ is hydrogen, as represented by structure (III):

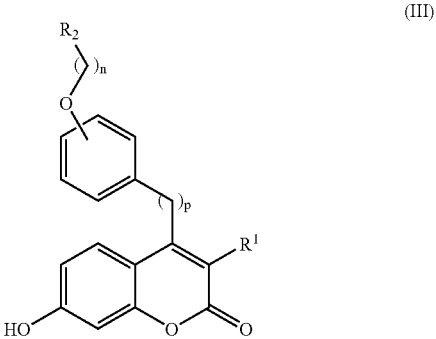

wherein $R_1$, $R_2$, n and p are as defined above.

In more specific embodiments of structures (II) and (III), representative compounds useful in the methods of this invention have the following structure (IV):

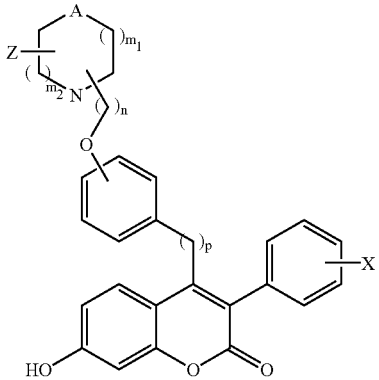

wherein A, X, Z, $m_1$, $m_2$, n and p are as defined above.

In a further embodiment of structure (IV), $m_1$, $m_2$ and p are 1; A is $CH_2$; the optional Z substituent is not present; n is 2; and compounds useful in the methods of this invention have the following structure (V):

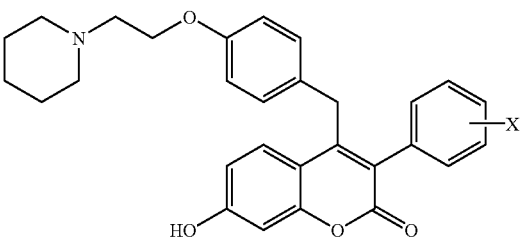

wherein X represents one or more optional substitutents as defined above.

In a more specific embodiment, the compounds useful for treating or preventing a primary brain cancer or a brain metastasis are those wherein X is either (a) not present or (b) present and represents a single substituent, such as a single substituent at the para position. Accordingly, representative compounds useful in the methods of this invention include (but are not limited to) compounds having the following structures (VIa) and (VIb):

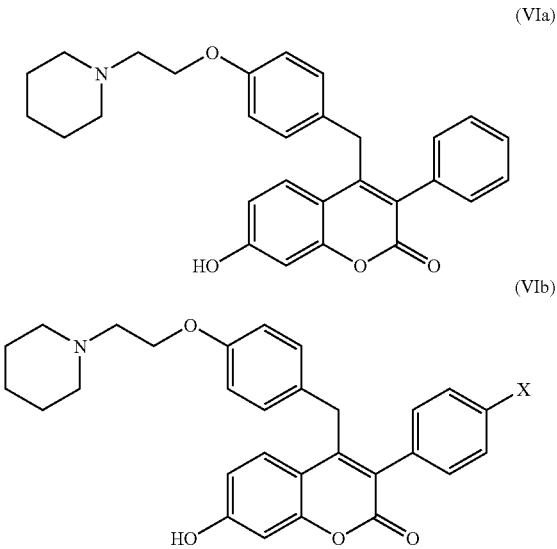

wherein X in structure (VIb) represents a halogen, preferably fluorine or chlorine.

A most preferable compound useful for treating or preventing a primary brain cancer or a brain metastasis has the following structure (VII):

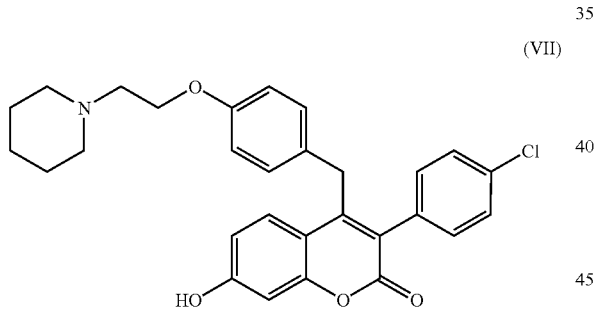

In a further embodiment of this invention, p is 0, and compounds useful in the methods of this invention have the following structure (VIII):

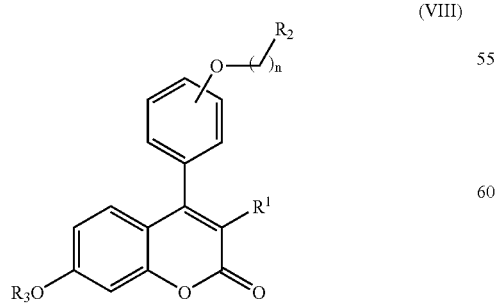

wherein $R_1$, $R_2$, $R_3$ and n are as defined above.

In one embodiment of structure (VIII), $R_1$ is an unsubstituted or substituted phenyl, and the compounds useful in the methods of this invention have the following structure (IX):

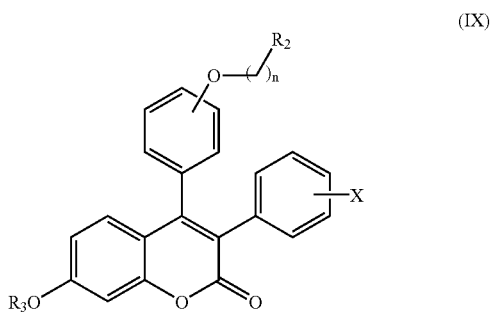

wherein X represents one or more optional substituents as defined above, and $R_2$, $R_3$ and n are as defined above.

In another embodiment, the compounds useful for treating or preventing a primary brain cancer or a brain metastasis are those wherein $R_3$ is hydrogen, as represented by structure (X):

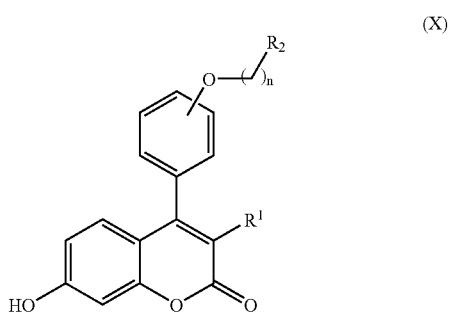

wherein $R_1$, $R_2$ and n are as defined above.

In more specific embodiments of structures (IX) and (X), representative compounds useful in the methods of this invention have the following structure (XI):

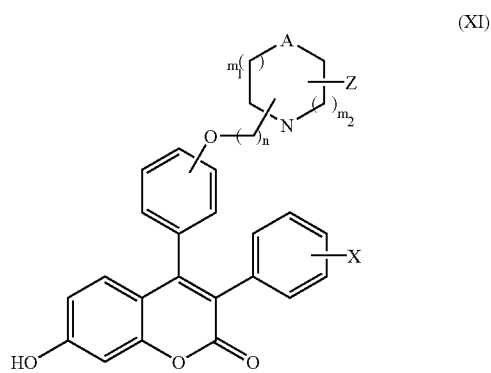

wherein A, X, Z, $m_1$, $m_2$, and n are as defined above.

In a further embodiment of structure (XI), $m_1$ and $m_2$ are 1, A is $CH_2$, the optional Z substituent is not present, and n is 2, and compounds useful in the methods of this invention have the following structure (XII):

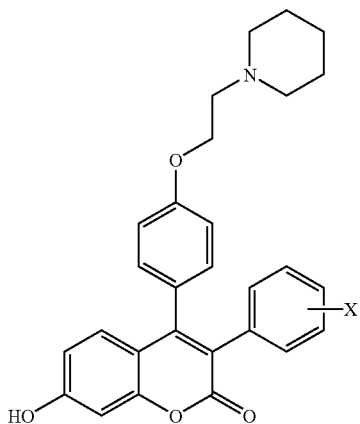

(XII)

wherein X represents one or more optional substitutents as defined above.

In a more specific embodiment, the compound s useful for treating or preventing a primary brain cancer or a brain metastasis are those wherein X is either (a) not present or (b) present and represents a single substituent, such as a single substituent at the para position. Accordingly, representative compounds useful in the methods of this invention include (but are not limited to) compounds having the following structures (XIIa) and (XIIb):

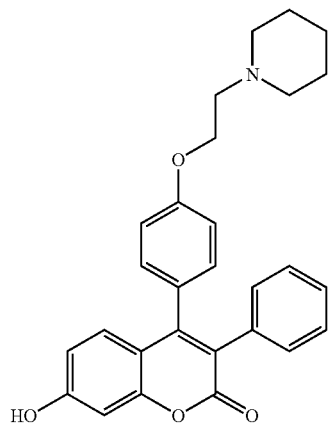

(XIIa)

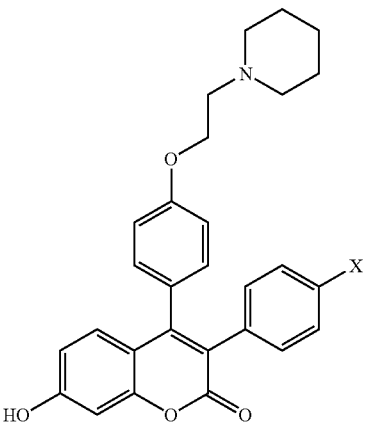

-continued (XIIb)

wherein X in structure (XIIb) represents a halogen, preferably fluorine or chlorine.

In certain embodiments, the cancers or metastasis to be treated or prevented in the present invention include, but are not limited to, primary intracranial central nervous system tumors. Primary intracranial central nervous system tumors include glioblastoma multiform; malignant astrocytomas; oligdendroglioma; ependymoma; low-grade astrocytomas; meningioma; mesenchymal tumors; pituitary tumors; nerve sheath tumors such as schwannomas; central nervous system lymphoma; medulloblastoma; primitive neuroectodermal tumors; neuron and neuron/glial tumors; craniopharyngioma; germ cell tumors; and choroid plexus tumors.

In other embodiments, the cancers or metastasis to be treated or prevented in the present invention include, but are not limited to, primary spinal tumors such as schwannoma, meningioma, ependymoma, sarcomas, astrocytoma, gliomas, vascular tumors, chordomas and epidermoids.

In other embodiments, the cancers or metastasis to be treated or prevented in the present invention include, but are not limited to, primary tumors responsible for brain metastasis such as lung (both small cell and non-small cell), breast, unknown primary, melanoma and colon.

4.1 Methods for Obtaining the Compounds

The compounds useful in the methods of this invention may be made by one skilled in organic synthesis by known techniques, as well as by the synthetic routes disclosed herein. For example, representative compounds of this invention may be synthesized by the following general Reaction Scheme 1:

Reaction Scheme 1

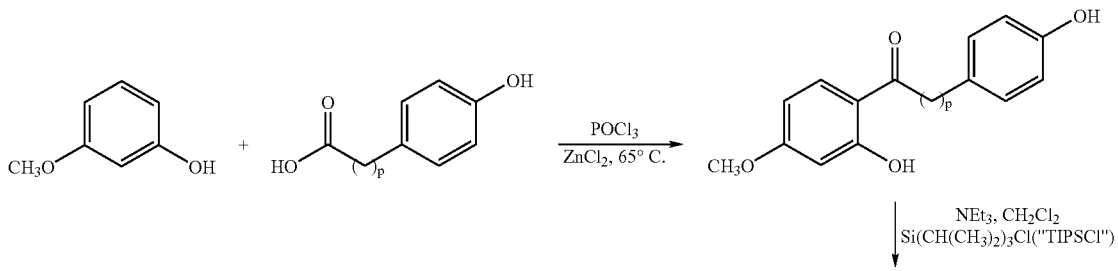

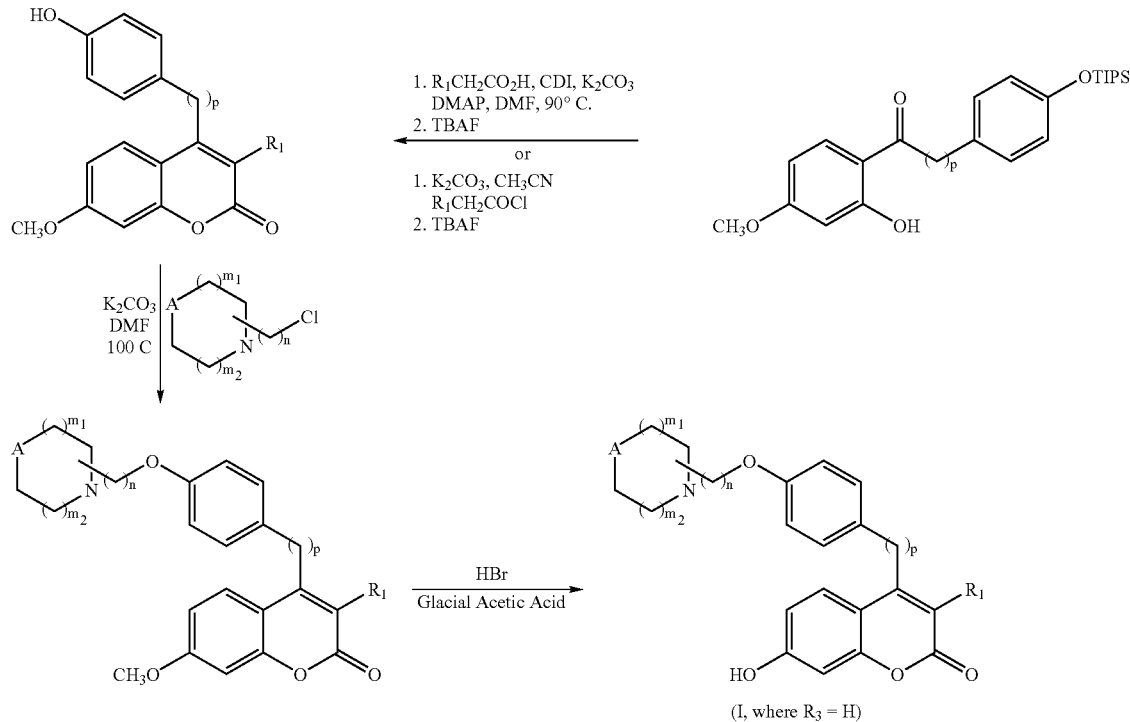

Reaction Scheme 1 yields compounds wherein $R_3$ is methyl or hydrogen, and $R_2$ is a heterocyclic ring as defined in structure (I). Further substitution at the $R_3$ position may be accomplished using an appropriately substituted phenol, or by subsequent conversion of the hydroxyl group (when $R_3$=H) using techniques known in the field of organic synthesis. Similarly, compounds of structure (I) wherein $R_2$ is $NR_aR_b$ may be made by employing the corresponding amino chloride, $R_aR_bN(CH_2)_nCl$, in place of the heterocyclic ring in the second-to-last step of Reaction Scheme 1.

More specifically, representative compounds useful in the methods of this invention (when $R_3$ is hydrogen and $R_2$ is piperid-1-yl) may be made by the following Reaction Scheme 2:

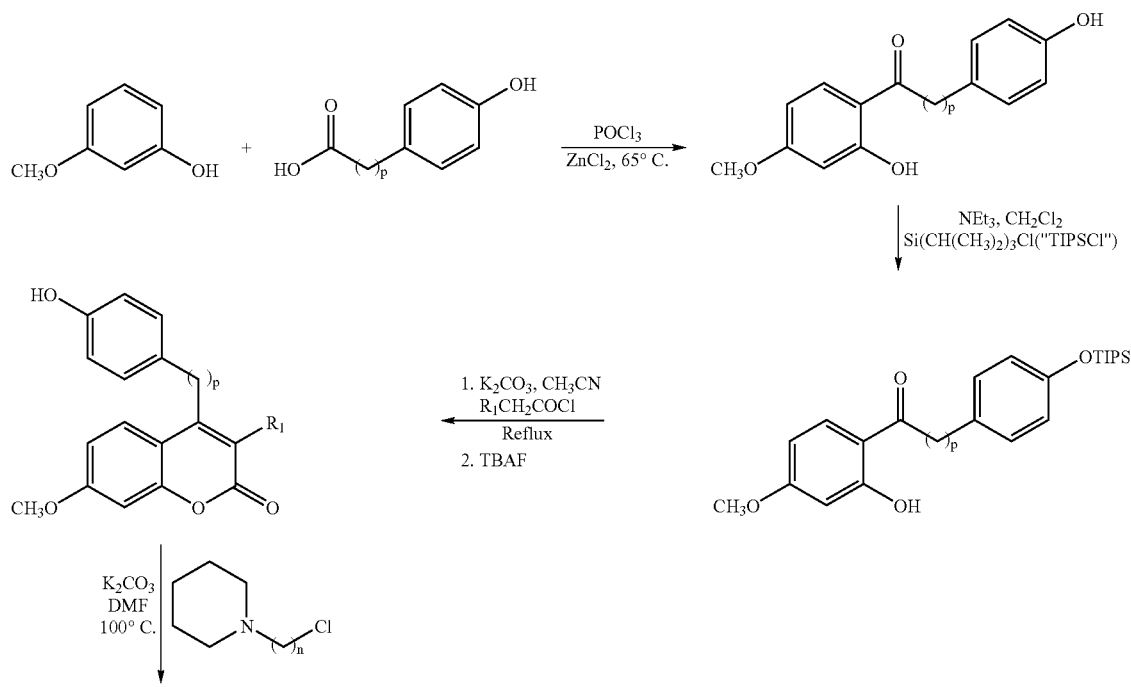

-continued

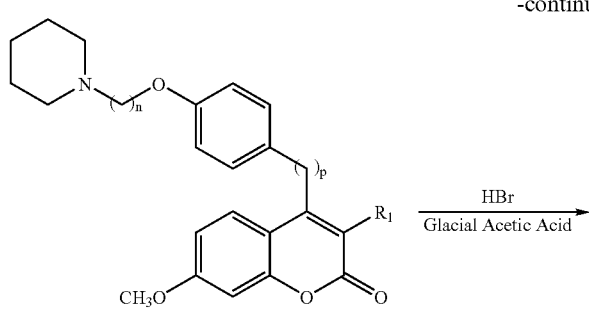 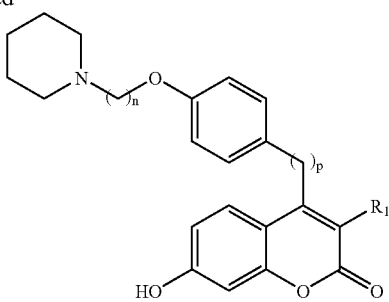

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

4.2 Therapeutic/Prophylactic Administration and Compositions

As used herein, the compounds (and pharmaceutically salts thereof) useful in the present methods are known collectively as "Benzopyranone-Type compounds".

Due to the activity of the Benzopyranone-Type compounds, the Benzopyranone-Type compounds are advantageously useful in veterinary and human medicine. In particular, the Benzopyranone-Type compounds are useful for the cancers or metastasis to be treated or prevented.

When administered to a patient, e.g., an animal for veterinary use or to a human for clinical use, the Benzopyranone-Type compounds are preferably in isolated form. By "isolated" it is meant that prior to administration, a Benzopyranone-Type compound is separated from other components of a synthetic organic chemical reaction mixture or natural product source, e.g., plant matter, tissue culture, bacterial broth, etc. Preferably, the Benzopyranone-Type compounds are isolated via conventional techniques, e.g., extraction followed by chromatography, recrystalization, or another conventional technique. When in isolated form, the Benzopyranone-Type compounds are at least 90%, preferably at least 95%, of a single Benzopyranone-Type compound by weight of that which is isolated. "Single Benzopyranone-Type compound" means an enantiomer or a racemate of a Benzopyranone-Type compound.

The invention provides methods of treatment or prevention by administration to a patient of an effective amount of a Benzopyranone-Type compound. The patient is preferably an animal, including, but not limited to, an animal such a cow, horse, sheep, pig, chicken, turkey, quail, cat, dog, mouse, rat, rabbit, guinea pig, etc., and is more preferably a mammal, and most preferably a human.

The Benzopyranone-Type compounds are advantageously administered in the form of a pharmaceutical composition. These compositions can be administered by any convenient route, for example by infusion or bolus injection, by absorption through epithelial or mucocutaneous linings (e.g., oral mucosa, rectal and intestinal mucosa, etc.) or via a convection-enhanced drug delivery system and may be administered together with another biologically active agent. Administration can be systemic or local. Various delivery systems are known, e.g., encapsulation in liposomes, microparticles, microcapsules, capsules, etc., and can be used to administer a Benzopyranone-Type compound of the invention. In certain embodiments, more than one Benzopyranone-Type compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the particular site of the medical condition.

In specific embodiments, it may be desirable to administer one or more Benzopyranone-Type compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the primary brain cancer or brain metastasis.

In certain embodiments, it may be desirable to introduce one or more Benzopyranone-Type compounds of the invention into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Benzopyranone-Type compounds can be formulated as a suppository, with traditional binders and carriers such as triglycerides.

In one embodiment, the Benzopyranone-Type compound is administered via a convection-enhanced drug delivery system. In another embodiment, the Benzopyranone-Type compound is administered via a convection-enhanced drug delivery system such as that described in U.S Pat. No. 5,720,720, incorporated by reference herein. Convection-enhanced drug delivery involves positioning the tip of an infusion catheter within a tissue (e.g., brain tissue) and supplying the drug (e.g., a Benzopyranone-Type compound) through the catheter while maintaining a positive pressure gradient from the tip of the catheter during infusion. The catheter is connected to a pump which delivers the drug and maintains the desired pressure gradient throughout delivery of the drug. Drug delivery rates are typically about 0.5 to about 4.0 µl/min with infusion distances of about 1 cm or more. This method is particularly useful for the delivery of drugs to the brain and other tissue, particularly solid nervous tissue. In certain embodiments, convection-enhanced drug delivery is useful for delivering a Benzopyranone-Type compound in combination with a high molecular-weight polar molecule such as growth factors, enzymes, antibodies, protein conjugates and genetic vectors to the brain or other tissue. In these embodiments, inflow rates can be up to about 15.0 µl/min.

In another embodiment, the Benzopyranone-Type compounds of the invention can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.).

In yet another embodiment, the Benzopyranone-Type compounds can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Benzopyranone-Type compounds, e.g, the brain, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) may be used.

The present compositions will contain an effective amount of a Benzopyranone-Type compound, preferably in purified form, preferably together with a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Benzopyranone-Type compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the Benzopyranone-Type compounds and pharmaceutically acceptable carriers are preferably sterile. Water is a preferred carrier when the Benzopyranone-Type compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

The phrase "pharmaceutically acceptable salt(s)," as used herein includes but are not limited to salts of acidic or basic groups that may be present in compounds used in the present methods and compositions. Compounds included in the present methods and compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present methods and compositions that include an amino moiety may form pharmaceutically or cosmetically acceptable salts with various amino acids, in addition to the acids mentioned above. Compounds, included in the present methods and compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

In a preferred embodiment, the Benzopyranone-Type compounds are formulated in accordance with routine procedures as a pharmaceutical composition adapted for intravenous administration to human beings. Typically, Benzopyranone-Type compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Benzopyranone-Type compound is to be administered by infusion, it can be dispensed, for example, with an infusion bottle containing sterile pharmaceutical grade water or saline. Where the Benzopyranone-Type compound is administered by injection, an ampoule of sterile water for injection or saline can be provided so that the ingredients may be mixed prior to administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Benzopyranone-Type compounds. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

The amount of the Benzopyranone-Type compound that will be effective in the treatment or prevention of a primary brain cancer or a brain metastasis can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, the general range of effective oral administration amounts of the compound is from about 0.5 mg/day to about 5000 mg/day, preferably about 500 mg/day to about 3500 mg/day, more preferably about 1000 mg/day to about 3000 mg/day, more preferably about 1500 mg/day to about 2500 mg/day and most preferably about 2000 mg/day. In another embodiment, effective amounts for intravenous administration are about 10% of an oral dosage amount and effective amounts for convection-enhanced drug administration are about 1% of an oral dosage amount. Of course, it is often practical to administer the daily dose of compound in portions, at various hours of the day. However, in any given case, the amount of compound administered will depend on such factors as the solubility of the active component, the formulation used and the route of administration. Suppositories generally contain active ingredient in the range of about 0.5% to about 10% by weight. Oral compositions preferably contain about 10% to about 95% active ingredient. In specific preferred embodiments of the invention, suitable dose ranges for oral administration are generally about 10–500 mg of active compound per kilogram body weight. In specific preferred embodiments, the oral dose is about 10–100, 100–300, 300–900, or 900–1500 mg per kilogram body weight. In other embodiments, the oral dose is about 100–200, 200–300, 300–400 or 400–500 mg per kilogram body weight. In other specific preferred embodiments of the invention, suitable dose ranges for oral administration are generally 1–7500 micrograms of active compound per kilogram body weight. In specific preferred embodiments, the oral dose is 1–10, 10–30, 30–90, or 90–150 micrograms per kilogram body weight. In other embodiments, the oral dose is 150–250, 250–325, 325–450, 450–1000 or 1000–7500 micrograms per kilogram body weight. Effective doses may be extrapolated from dose-response curves derived from in vitro or animal model test systems. Such animal models and systems are well known in the art.

The invention also provides pharmaceutical packs or kits comprising one or more containers filled with one or more Benzopyranone-Type compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In certain preferred embodiments, the kit may also contain one or more other chemotherapeutic agents useful for treating or preventing a primary brain cancer or a brain metastasis to be administered in combination with a Benzopyranone-Type compound of the invention.

The Benzopyranone-Type compounds useful in the methods and compositions of the invention are preferably assayed in vitro, and then in vivo, for the desired therapeutic or prophylactic activity, prior to use in humans. For example, in vitro assays can be used to determine whether administration of a specific Benzopyranone-Type compound or combination of Benzopyranone-Type compounds is preferred.

In one embodiment, a patient tissue sample is grown in culture, and contacted or otherwise administered with a Benzopyranone-Type compound, and the effect of such Benzopyranone-Type compound upon the tissue sample is observed and compared to a non-contacted tissue. In other embodiments, a cell culture model is used in which the cells of the cell culture are contacted or otherwise administered with a Benzopyranone-Type compound, and the effect of such Benzopyranone-Type compound upon the tissue sample is observed and compared to a non-contacted cell culture. Generally, a lower level of proliferation or survival of the contacted cells compared to the non-contracted cells indicates that the Benzopyranone-Type compound is effective to treat a the patient. Such Benzopyranone-Type compounds may also be demonstrated effective and safe using animal model systems.

Other methods will be known to the skilled artisan and are within the scope of the invention.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash in the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A typical technique for preparing hydrochlorides is to dissolve the free base in a suitable solvent and dry the solution thoroughly, as over molecular sieves, before bubbling hydrogen chloride gas through it.

4.3 Inhibition of Cancer and Neoplastic Cells and Disease

The Benzopyranone-Type compounds can be demonstrated to inhibit primary brain cancer and brain metastasis tumor cell proliferation, cell transformation and tumorigenesis in vitro and in vivo using a variety of assays known in the art, or described herein. Such activity can be demonstrated in an in vitro assay by contacting the Benzopyranone-Type compounds of the present invention with glioma tumor cells. In general, glioma tumor cells are exposed to varying concentrations of the Benzopyranone-Type compounds, followed by measuring cell survival relative to controls (Manome, Y. et al. (1996) Gene Therapy for Malignant Gliomas Using Replication Incompetent Retroviral and Adenoviral Vectors Encoding the Cytochrome P450 2B1 Gene Together With Cyclophosphamide, *Gene Therapy* 3:513–520). Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g. ,fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell-cycle marker antibodies are from Santa Cruz Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell-cycle and cell-proliferation analysis by a variety of techniques known in the art, including but not limited to the following:

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using ($^3$H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189–199; Vassilev et al., 1995, J. Cell Sci. 108:1205–15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, T., et al., 1998, Prostate 34:175–81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol.135:783–92). In an another embodiment, DNA content may be analyzed by preparation of a chromosomal spread (Zabalou, S., 1994, Hereditas.120: 127–40; Pardue, 1994, Meth. Cell Biol. 44:333–351).

The expression of cell-cycle proteins (e.g., CycA, CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., 1993, Cell 75:805–816; Li et al., 1996, Curr. Biol. 6:189–199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell-cycle or speed of cell-cycle may also be used to measure inhibition of cell proliferation by the Benzopyranone-Type compounds. In one embodiment the length of the cell-cycle is determined by the doubling time of a population of cells (e.g., using cells contacted or not contacted with one or more Benzopyranone-Type compounds of the invention). In another embodiment, FACS analysis is used to analyze the phase of cell-cycle progression, or purify G1, S, and G2/M fractions (see e.g., Delia, D. et al., 1997, Oncogene 14:2137–47).

Lapse of cell-cycle checkpoint(s), and/or induction of cell-cycle checkpoint(s), may be examined by the methods described herein, or by any method known in the art. Without limitation, a cell-cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63–80). Induction or inhibition of cell-ycle checkpoint genes may be assayed, for example, by Western blot analysis, or by immunostaining, etc. Lapse of cell-cycle checkpoints may be further assessed by the progression of a cell through the checkpoint without prior occurrence of specific events (e.g. progression into mitosis without complete replication of the genomic DNA).

In addition to the effects of expression of a particular cell-cycle protein, activity and post-translational modifications of proteins involved in the cell-cycle can play an integral role in the regulation and proliferative state of a cell. The invention provides for assays involved detected post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485–91; Paige, L., 1988, Biochem J.;250:485–91).

Activity of signaling and cell cycle proteins and/or protein complexes is often mediated by a kinase activity. The present invention provides for analysis of kinase activity by assays such as the histone H1 assay (see e.g, Delia, D. et al., 1997, Oncogene 14:2137–47).

The Benzopyranone-Type compounds can also be demonstrated to alter cell-proliferation in cultured cells in vitro using methods which are well known in the art. Specific examples of cell-culture models for primary brain cancer and brain metastasis include, but are not limited to, those found in the following U.S. Patents: U.S. Pat. Nos. 6,194,158; 6,051,376 and 6,071,696.

The Benzopyranone-Type compounds can also be demonstrated to inhibit cell transformation (or progression to malignant phenotype) in vitro. In this embodiment, cells with a transformed cell phenotype are contacted with one or more Benzopyranone-Type compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436–446).

Loss of invasiveness or decreased adhesion may also be used to demonstrate the anti-cancer effects of the Benzopyranone-Type compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278: 1464–66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464–66).

Alternatively, loss of invasiveness may be measured by cell migration through a chemotaxis chamber (Neuroprobe/Precision Biochemicals Inc. Vancouver, B C). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun.193:518–25).

The Benzopyranone-Type compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine*, 13th Edition, Isselbacher et al., eds., McGraw-Hill, New York, p. 1814, and Lovejoy et al., 1997, J. Pathol. 181:130–135). Specific examples for primary brain cancer and brain metastasis can be found in the following U.S. Patents: U.S. Pat. Nos. 5,894,018; 6,028,174 and 6,203,787. Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25–F48), and immune responses to tumors in rat (Frey, 1997, Methods, 12:173–188).

For example, a Benzopyranone-Type compound can be administered to a test animal, preferably a test animal predisposed to develop a glioblastoma multiform, and the test animal subsequently examined for an decreased incidence of tumor formation in comparison with controls not administered the Benzopyranone-Type compound. Alternatively, a Benzopyranone-Type compound can be administered to test animals having glioblastoma multiform tumors (e.g., animals in which tumors have been induced by introduction of malignant, neoplastic, or transformed cells, or by administration of a carcinogen) and subsequently examining the tumors in the test animals for tumor regression in comparison to controls not administered the Benzopyranone-Type compound.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in Formulation or minor changes in experimental design, are to be considered to fall within the scope of the invention incorporated herein.

5. EXAMPLES

In summary, Examples 1–11 are directed to the synthesis of representative compounds of this invention.

Example 1

2-(4-HYDROXYBENZYLACETONE)-5-METHOXYPHENOL

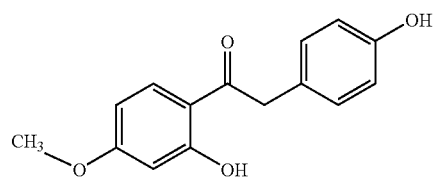

To a mixture of 3-methoxyphenol (50 g, 0.40 mol), 4-hydroxyphenylacetic acid (71 g, 0.46 mol) and $ZnCl_2$ (174 g, 1.28 mol) was added $POCl_3$ (100 ml, 1.6 mol). The mixture was stirred at 65° C. for 2 hours, poured into ice water (2 L) and stirred until the ice melted. The clear supernatant was decanted and the residue was rinsed with water (1 L) and partitioned between EtOAc and water. The organic layer was washed with brine, dried ($MgSO_4$), filtered and concentrated. The resulting oil was purified by chromatography ($SiO_2$, 20% EtOAc/n-hexane) to provide 2-(4-hydroxybenzylacetone)-5-methoxyphenol (34.1 g, 33% yield) as a white solid; mp 137–140° C.

Example 2

2-(4-TRIISOPROPYLSILYLOXYBENZYLAC-ETONE)-5-METHOXYPHENOL

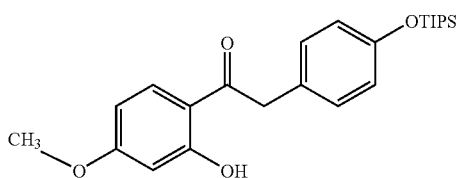

To a mixture of 2-(4-hydroxybenzylacetone)-5-methoxyphenol (10 g, 0.038 mole), $NEt_3$ (6 ml, 0.042 mole) in $CH_2Cl_2$ (50 ml) was added triisopropylsilylchloride (9 ml, 0.042 mole). The mixture was stirred for 22 hours, concentrated and the residue partitioned between EtOAc and $H_2O$. The organic layer was washed with NaOH (1N), HCl (1N) and brine. The organic layer was dried ($MgSO_4$), filtered and concentrated. The residue was reated with n-hexane to provide 2-(4-triisopropylsilyloxybenzylacetone)-5-methoxyphenol 6.2 g, 38% yield) as a white solid; mp 66–68° C.

Example 3

3-PHENYL-4-(4-HYDROXYBENZYL)-7-METHOXYCOUMARIN

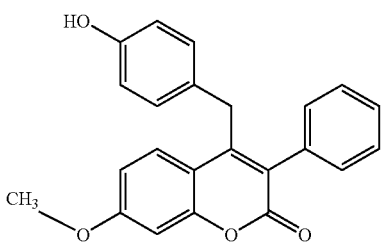

To a mixture of 2-(4-triisopropylsilyloxybenzylacetone)-5-methoxyphenol (4 g, 9.6 mmole), $K_2CO_3$ (4 g, 29 mmole) in $CH_3CN$ (50 ml) was added phenyl acetylchloride (2.3 ml, 14 mmole). The mixture was stirred at reflux for 22 hrs, poured into $H_2O$ (0° C.) (500 ml) and extracted with EtOAc (2×). The organic layer was dried ($MgSO_4$), filtered and concentrated. The residue was stirred with $Et_2O$ and the resulting solid was filtered and recrystallized (EtOH) to give 3-phenyl-4-(4-hydroxybenzyl)-7-methoxycoumarin (0.88 g, 15% yield) as a white solid; mp 235–236° C.

Example 4

3-PHENYL-4-[4-(2-{PIPERIN-1-YL})ETHOXY]-BENZYL-7-METHOXYCOUMARIN

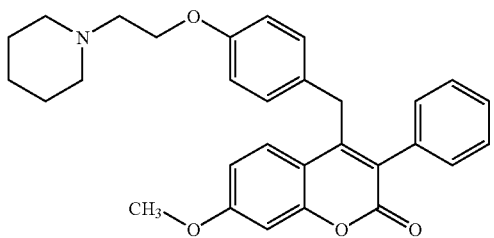

A mixture of 3-phenyl-4-(4-hydroxybenzyl)-7-methoxycoumarin (0.50 g, 1.39 mmoles), $K_2CO_3$ (0.58 g, 4.18 mmoles), 2-chloroethylpiperdine hydrochloride (0.41 g, 2.22 mmoles) and acetone (50 ml) was heated at reflux for 6 hours. The solvent was concentrated to a solid which was partitioned between EtOAc and $H_2O$. The organic layer was washed with NaOH (1H), brine, dried ($MgSO_4$), filtered and concentrated. The residue was stirred with HCl (20% in EtOAc) and the solid filtered to provide 3-phenyl-4-[4-(2-{piperin-1-yl})ethoxy]-benzyl-7-methoxycoumarin (0.57 g, 87% yield); mp 171–172° C.

Example 5

3-PHENYL-4-[4-(2-{PIPERIDIN-1-YL})ETHOXY]-BENZYL-7-HYDROXYCOUMARIN

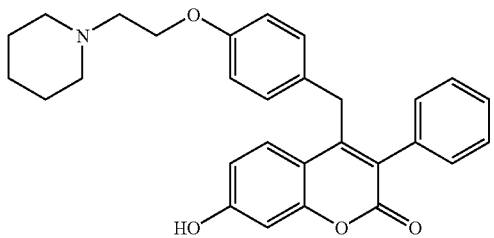

A mixture of 3-phenyl-4-[4-(2-{piperin-1-yl})ethoxy]-benzyl-7-methoxycoumarin (0.10 g, 0.20 mmole), HOAc (glacial) (15 ml) and HBr (48%, 15 ml) was refluxed for 48 hours. The mixture was partitioned between EtOAc (120 ml) and NaOH (1N, 120 ml) and the aqueous layer was washed with EtOAc. The aqueous layer was then acidified (conc. HCl, pH 1–2) and filtered to provide 3-phenyl-4-[4-(2-{piperidin-1-yl})ethoxy]-benzyl-7-hydroxycoumarin (0.88 g, 99% yield); mp 160–161° C.

Example 6

3-(4-FLUOROPHENYL)-4-[4-(1-METHYLPIP-ERIDYL-3-OXY)]-BENZYL-7-HYDROXYCOUMARIN

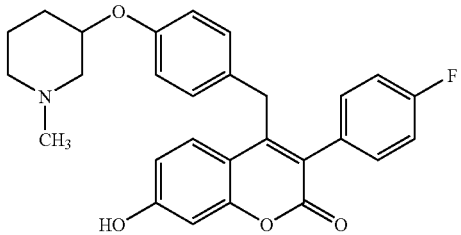

A solution of 3-(4-fluorophenyl)-4-[(4-hydroxyphenyl)methyl]-7-methoxy-2H-chromen-2-one (0.27 g, 0.72 mmole), in 3 mL of CH$_2$Cl$_2$ was treated with 3-hydroxy-1-methylpiperidine (0.42 g, 3.6 mmol), triphenyiphosphine (0.94 g, 3.6 mmol), and diethyl azodicarboxylate (0.65 g, 3.6 mmol). The reaction mixture was stirred for 8 hours at 25° C. then concentrated under reduced pressure. The crude product was dissolved in 4 mL of a 1:1 solution of HBr (48%, aqueous) and glacial acetic acid. The resulting solution was warmed at 90° C. for 12 hours. The reaction mixture was concentrated and the resulting residue was neutralized with 10 mL of saturated aqueous NaHCO$_3$. The aqueous mixture was extracted with CH$_2$Cl$_2$ (3×15 mL) and the combined organic layer was dried (MgSO$_4$) then concentrated under reduced pressure. The product (106 mg, 32%) was isolated following purification by flash chromatography (SiO$_2$, CH$_2$Cl$_2$/MeOH, 10:1).

Alternatively, 3-(4-fluorophenyl)-4-[(4-hydroxyphenyl)methyl]-7-methoxy-2H-chromen-2-one is reacted with one of the following enantiomers (a) or (b) in the presence of PPh3 and diethyl azodicarboxylate (DEAD), followed by HBr/HOAc, to yield the corresponding enantiomeric product.

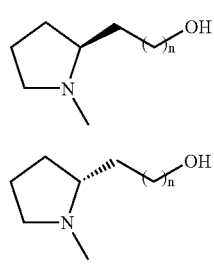

Example 7

2-HYDROXY-4-METHOXYPHENYL-4-HYDROXYPHENYL

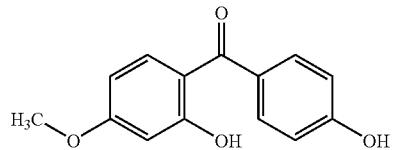

A solution of 3-methoxyphenol (2.5 g, 20.14 mmol), 4-hydroxybenzoic acid (3.2 g, 23.16 mmol), and ZnCl$_2$ (8.78 g, 64.44 mmol) in 15 mL of POCl$_3$ was warmed 65° C. for 2 hours. The resulting reaction mixture was poured onto ice water, (100 mL). The aqueous layer was extracted with CH$_2$Cl$_2$ and the combined organic layer was dried (MgSO$_4$) then concentrated under reduced pressure. The crude product purified by flash chromatography to provide the title compound (3.93 g, 80%) as an off-white solid (LC/MS=244 (M+H$^+$)).

Example 8

3-(4-CHLOROPHENYL)-4-(4-HYDROXYPHENYL)-7-METHOXY-2H-CHROMEN-2-ONE

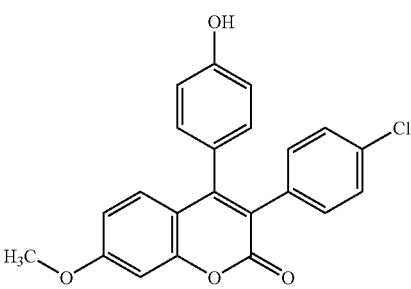

A suspension of 2-hydroxy-4-methoxyphenyl-4-hydroxyphenyl ketone (2.6 grams, 10.65 mmol), 4-chlorophenylacetic acid (4.0 g, 23.43 mmol), K$_2$CO$_3$ (4.4 g, 31.95 mnol), carbonyldiimidazole (3.8 g, 23.43 m.mol), and 4-dimethylaminopyridine (0.1 g) in 20 mL of DMF was warmed at 90° C. for 5 hours. The reaction mixture was poured into 150 mL of H$_2$O and stirred for 30 minutes. The precipitated product was collected by filtration and the purified desired product was isolated following flash chromatography (2.1 g, 52%, LC/MS=379 (M+H$^+$)).

Example 9

3-(4-CHLOROPHENYL)-7-METHOXY-4-[4-(2-PIPERIDYLETHOXY)PHENYL]-2H-CHROMEN-2-ONE

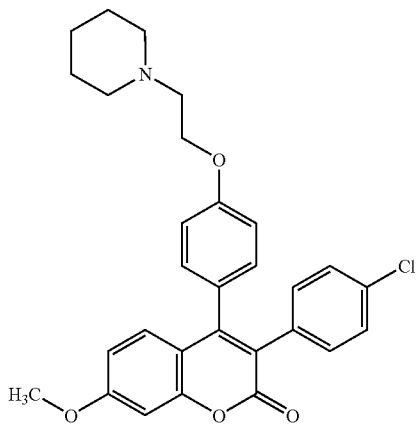

The title compound was prepared from 3-(4-chlorophenyl)-4-(4hydroxyphenyl)-7-methoxy-2H-chromen-2-one as described in Example 4 (LC/MS=492 (M+H$^+$)).

Example 10

3-(4-CHLOROPHENYL)-7-HYDROXY-4-[4-(2-PIPERIDYLETHOXY)PHENYL]-2H-CHROMEN-2-ON

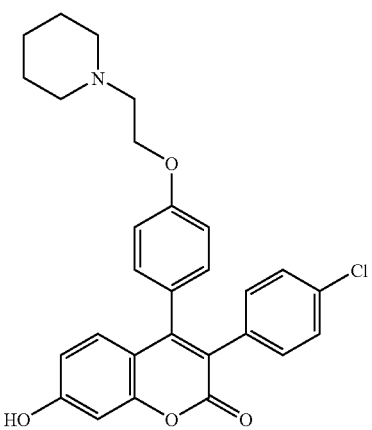

The title compound was prepared from 3-(4-chlorophenyl)-7-methoxy-4-[4-(2-piperidylethoxy)phenyl]-2H-chromen-2-one as described in Example 5 (LC/MS=476 (M+H$^+$)).

Example 11

ADDITIONAL REPRESENTATIVE COMPOUNDS

By the procedures set forth herein, the compounds of Table 1 may be prepared.

TABLE 1

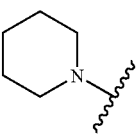

Representative Compounds

| No. | $R_1$ | $R_2$† | $R_3$ | n | p | LC/MS (M + H$^+$) |
|---|---|---|---|---|---|---|
| 1 | Phenyl | piperidine | H | 2 | 1 | 456 |

TABLE 1-continued
Representative Compounds
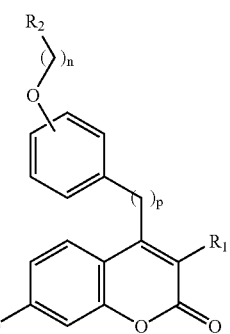
| No. | R₁ | R₂† | R₃ | n | p | LC/MS (M + H⁺) |
|---|---|---|---|---|---|---|
| 2 | 4-fluorophenyl | piperidinyl | H | 2 | 1 | 474 |
| 3 | 4-chlorophenyl | piperidinyl | H | 2 | 1 | 490 |
| 4 | 4-bromophenyl | piperidinyl | H | 2 | 1 | 533, 535 |
| 5 | 3-chlorophenyl | piperidinyl | H | 2 | 1 | 490 |
| 6 | 2-chlorophenyl | piperidinyl | H | 2 | 1 | 490 |
| 7 | 3-methylphenyl | piperidinyl | H | 2 | 1 | 470 |
| 8 | 2-methylphenyl | piperidinyl | H | 2 | 1 | 470 |
| 9 | 4-methylphenyl | piperidinyl | H | 2 | 1 | 470 |

TABLE 1-continued
Representative Compounds
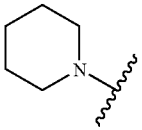
| No. | R₁ | R₂† | R₃ | n | p | LC/MS (M + H⁺) |
|---|---|---|---|---|---|---|
| 10 | 4-hydroxyphenyl | 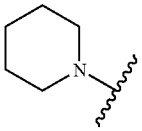 | H | 2 | 1 | 473 |
| 11 | 5-bromopyridin-3-yl | 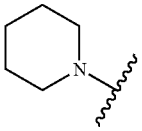 | H | 2 | 1 | 535, 537 |
| 12 | 3,4-dichlorophenyl | 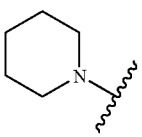 | H | 2 | 1 | 524, 526 |
| 13 | Thiophen-2-yl | 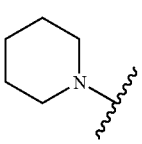 | H | 2 | 1 | 462 |
| 14 | 4-trifluormethylphenyl | 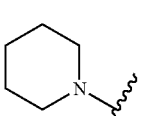 | H | 2 | 1 | 524 |
| 15 | 4-chlorophenyl | 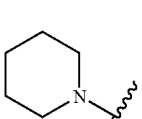 | H | 2 | 2 | 504 |
| 16 | 4-chlorophenyl | 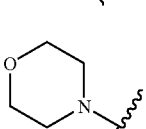 | H | 2 | 0 | 476 |
| 17 | Phenyl |  | H | 2 | 1 | 458 |

TABLE 1-continued

Representative Compounds

| No. | R₁ | R₂† | R₃ | n | p | LC/MS (M + H⁺) |
|---|---|---|---|---|---|---|
| 18 | 4-fluorophenyl | N-methylpyrrolidin-2-yl | H | 2 | 1 | 474 |
| 19 | Phenyl | piperidin-1-yl | SO₂N(CH₃)₂ | 2 | 1 | 563 |
| 20 | Phenyl | piperidin-1-yl | CON(CH₃)₂ | 2 | 1 | 527 |
| 21 | Phenyl | piperidin-1-yl | CO(phenyl) | 2 | 1 | 560 |
| 22 | Phenyl | piperidin-1-yl | COCH₃ | 2 | 1 | 498 |
| 23 | Phenyl | piperidin-1-yl | COOCH₂CH₃ | 2 | 1 | 528 |
| 24 | 4-fluorophenyl | piperidin-1-yl | CH₂CH₂CH₂-piperidin-1-yl | 2 | 1 | 585 |
| 25 | 4-fluorophenyl | piperidin-1-yl | CH₂CH₂N(CH₃)₂ | 2 | 1 | 574 |

TABLE 1-continued

Representative Compounds

| No. | R₁ | R₂† | R₃ | n | p | LC/MS (M + H⁺) |
|---|---|---|---|---|---|---|
| 26 | 4-chlorophenyl | piperidinyl (N-linked, with + charges) | H | 2 | 1 | 490 |
| 27 | 4-chlorophenyl | 1-methylpyrrolidin-2-yl | H | 2 | 1 | 490 |
| 28 | 4-fluorophenyl | 1-benzylimidazol-2-yl | H | 1 | 1 | 533 |
| 29 | 4-fluorophenyl | imidazol-1-yl | H | 2 | 1 | 457 |
| 30 | 4-fluorophenyl | 1-methylpiperidin-3-yl | H | 0 | 1 | 460 |
| 31 | 4-fluorophenyl | 1-methylpyrrolidin-2-yl | H | 1 | 1 | 460 |
| 32 | 4-fluorophenyl | 1-methylpiperidin-4-yl | H | 0 | 1 | 460 |

TABLE 1-continued
Representative Compounds
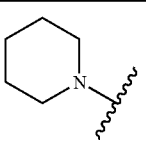
| No. | R₁ | R₂† | R₃ | n | p | LC/MS (M + H⁺) |
|---|---|---|---|---|---|---|
| 33 | 4-chlorophenyl | 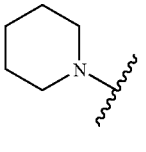 | SO$_2$NH$_2$ | 2 | 1 | 570 |
| 34 | 2,4-difluorophenyl | 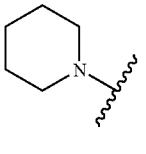 | H | 2 | 1 | 492 |
| 35 | 2,4-dichlorophenyl | 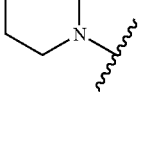 | H | 2 | 1 | 524 |
| 36 | 4-chlorophenyl | 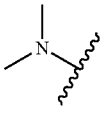 | SO$_2$CH$_3$ | 2 | 1 | 568 |
| 37 | 4-fluorophenyl | 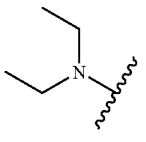 | H | 3 | 1 | 448 |
| 38 | Phenyl | 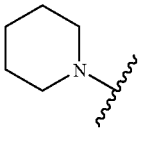 | H | 2 | 0 | 430 |
| 39 | 4-chlorophenyl | 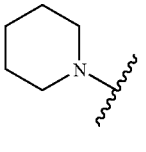 | CH$_3$ | 2 | 0 | 490 |

TABLE 1-continued
Representative Compounds

| No. | $R_1$ | $R_2$† | $R_3$ | n | p | LC/MS $(M + H^+)$ |
|---|---|---|---|---|---|---|
| 40 | 4-chlorophenyl | (2-pyrrolidinyl) | H | 2 | 0 | 462 |
| 41 | 4-chlorophenyl | (1-methyl-2-pyrrolidinyl) | H | 2 | 0 | 476 |
| 42 | 4-chlorophenyl | (piperidin-1-yl) | H | 3 | 0 | 490 |
| 43 | 4-chlorophenyl | (piperidin-1-yl) | H | 3 | 0 | 490 |

†At the 4-position of the phenyl ring unless otherwise noted
‡At the 3-position of the phenyl ring The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method for treating a glioma, comprising administering to a patient in need thereof an effective amount of a compound of the formula:

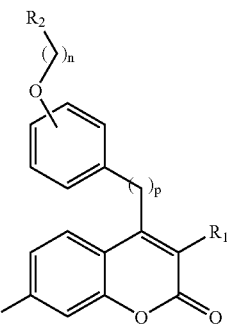

or a pharmaceutically acceptable salt thereof, wherein:

n is 0, 1, 2, 3 or 4;

p is 0, 1 or 2;

$R_1$ is an unsubstituted or substituted $C_{6-12}$aryl, $C_{7-12}$arylalkyl, $C_{3-12}$heterocycle or $C_{4-16}$heterocyclealkyl;

$R_2$ is $NR_aR_b$ wherein $R_a$ and $R_b$ are independently hydrogen, $C_{1-8}$alkyl, $C_{6-12}$aryl, or heterocycle, and wherein $R_a$ and $R_b$ are optionally substituted with up to three substituents independently selected from $C_{1-6}$alkyl, halogen, $C_{1-6}$alkoxy, hydroxy and carboxyl;

or $R_2$ is a heterocyclic ring of the following structure:

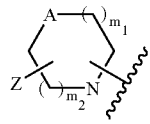

wherein $m_1$ and $m_2$ are independently 0, 1 or 2, and both of $m_1$ and $m_2$ are not 0, A is $CH_2$, O, S or NH, Z represents 0, 1, 2 or 3 heterocyclic ring substituents selected from halogen, $C_{1-8}$alkyl, $C_{6-12}$aryl, $C_{7-12}$arylalky, $C_{3-12}$heterocycle, or $C_{4-16}$heterocyclealkyl, and wherein any hydrogen atom on the heterocyclic ring may, taken together with a hydrogen atom on an adjacent atom of the heterocylic ring, form a double bond;

$R_3$ is hydrogen, $R_4$, $C(=O)R_4$, $C(=O)OR_4$, $CONHR_4$, $CONR_4R_5$, or $SO_2NR_5R_5$;

$R_4$ and $R_5$ are independently $C_{1-8}$alkyl, $C_{6-12}$aryl, $C_{7-12}$aralkyl, or a five- or six-membered heterocycle containing up to two heteroatoms selected from O, $NR_6$ and $S(O)_q$, wherein each of the above groups are optionally substituted with one to three substituents independently selected from $R_7$ and q is 0, 1 or 2;

$R_6$ is hydrogen or $C_{1-4}$alkyl; and $R_7$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $CONHOR_8$, $SO_2NHR_8$, $NH_2$, $C_{1-4}$alkylamino, $C_{1-4}$dialkylamino, $NHSO_2R_8$, $NO_2$, or a five- or six-membered heterocycle, where each occurrence of $R_8$ is independently $C_{1-6}$alkyl.

2. The method of claim 1 wherein $R_1$ is an unsubstituted or substituted $C_{6-12}$ aryl.

3. The method of claim 2 wherein $R_1$ is an unsubstituted or substituted phenyl.

4. The method of claim 3 wherein $R_1$ is an unsubstituted phenyl.

5. The method of claim 3 wherein $R_1$ is substituted phenyl.

6. The method of claim 5 wherein $R_1$ is 4-halophenyl, 4-methylphenyl, 4-hydroxyphenyl, 4-trifluorophenyl, 3-halophenyl, 2-halophenyl, 2,4-dihalophenyl, 3,4-dihalophenyl, wherein halo is fluoro, chloro, bromo or iodo.

7. The method of claim 1 wherein $R_1$ is an unsubstituted or substituted heteroaryl.

8. The method of claim 7 wherein $R_1$ is an substituted or unsubstituted pyridinyl or thiophenyl.

9. The method of claim 1 wherein $R_1$ is an unsubstituted or substituted $C_{7-12}$arylalkyl.

10. The method of claim 9 wherein $R_1$ is an unsubstituted or substituted benzyl.

11. The method of claim 1 wherein $R_1$ is an unsubstituted or substituted $C_{3-12}$heterocycle or $C_{4-16}$heterocyclealkyl.

12. The method of claim 1 wherein n is 2.

13. The method of claim 1 wherein n is 0, 1, 3 or 4.

14. The method of claim 1 wherein $R_3$ is hydrogen.

15. The method of claim 1 wherein $R_3$ is $C(=O)(C_{1-8}$alkyl) or $C(=O)(C_{6-12}$aryl).

16. The method of claim 1 wherein $R_3$ is $C(=O)O(C_{1-8}$alkyl), $SO_2NH_2$ or $CONH_2$.

17. The method of claim 1 wherein $R_2$ is a heterocyclic ring of the following structure:

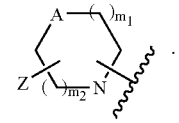

18. The method of claim 17 wherein $m_1$ and $m_2$ are 1.

19. The method of claim 18 wherein A is $CH_2$.

20. The method of claim 19 wherein $R_2$ is piperdin-1-yl.

21. The method of claim 18 wherein A is O.

22. The method of claim 21 wherein $R_2$ is morpholin-4-yl.

23. The method of claim 17 wherein $m_1$ is 1 and $m_2$ is 0.

24. The method of claim 23 wherein A is $CH_2$ and $R_2$ is imidazolidin-2-yl substituted with 0 or 1 Z substituents.

25. The method of claim 17 wherein $R_2$ is imidazol-1-yl or imidazol-2-yl substituted with 0 or 1 Z substituents.

26. The method of claim 1 wherein the $R_2$—$(CH_2)_n$—O— moiety is attached at the 4-position of the phenyl ring.

27. The method of claim 1 wherein the $R_2$—$(CH_2)_n$—O— moiety is attached at the 3-position of the phenyl ring.

28. The method of claim 1 wherein the glioma is glioblastoma multiforme; malignant astrocytomas; oligdendroglioma; ependymoma; or low-grade astrocytomas.

29. A method for treating a primary spinal tumor comprising administering to a patient in need thereof an effective amount of a compound of the formula:

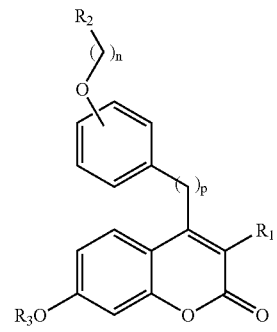

or a pharmaceutically acceptable salt thereof, wherein:

n is 0, 1, 2, 3 or 4;

p is 0, 1 or 2;

$R_1$ is an unsubstituted or substituted $C_{6-12}$aryl, $C_{7-12}$arylalkyl, $C_{3-12}$heterocycle or $C_{4-16}$heterocyclealkyl;

$R_2$ is $NR_aR_b$ wherein $R_a$ and $R_b$ are independently hydrogen, $C_{1-8}$alkyl, $C_{6-12}$aryl, or heterocycle, and wherein $R_a$ and $R_b$ are optionally substituted with up to three substituents independently selected from $C_{1-6}$alkyl, halogen, $C_{1-6}$alkoxy, hydroxy and carboxyl;

or $R_2$ is a heterocyclic ring of the following structure:

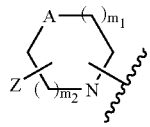

wherein $m_1$ and $m_2$ are independently 0, 1 or 2, and both of $m_1$ and $m_2$ are not 0, A is $CH_2$, O, S or NH, Z represents 0, 1, 2 or 3 heterocyclic ring substituents selected from halogen, $C_{1-8}$alkyl, $C_{6-12}$aryl, $C_{7-12}$aralkyl, $C_{3-12}$heterocycle, or $C_{4-16}$heterocyclealkyl, and wherein any hydrogen atom on the heterocyclic ring may, taken together with a hydrogen atom on an adjacent atom of the heterocylic ring, form a double bond;

$R_3$ is hydrogen, $R_4$, $C(=O)R_4$, $C(=O)OR_4$, $CONHR_4$, $CONR_4R_5$, or $SO_2NR_5R_5$;

$R_4$ and $R_5$ are independently $C_{1-8}$alkyl, $C_{6-12}$aryl, $C_{7-12}$aralkyl, or a five- or six-membered heterocycle containing up to two heteroatoms selected from O, $NR_6$ and $S(O)_q$, wherein each of the above groups are optionally substituted with one to three substituents independently selected from $R_7$ and q is 0, 1 or 2;

$R_6$ is hydrogen or $C_{1-4}$alkyl; and $R_7$ is hydrogen, halogen, hydroxy, $C_{1-6}$alkyl, $C_{1-4}$alkoxy, $C_{1-4}$acyloxy, $C_{1-4}$thio, $C_{1-4}$alkylsulfinyl, $C_{1-4}$alkylsulfonyl, (hydroxy)$C_{1-4}$alkyl, $C_{6-12}$aryl, $C_{7-12}$aralkyl, COOH, CN, $CONHOR_8$, $SO_2NHR_8$, $NH_2$, $C_{1-4}$alkylamino, $C_{1-4}$dialkylamino, $NHSO_2R_8$, $NO_2$, or a five- or six-membered heterocycle, where each occurrence of $R_8$ is independently $C_{1-6}$alkyl.

30. The method of claim 29 wherein the primary spinal tumor is schwannoma, meningioma, ependymoma, sarcomas, astrocytoma, gliomas, vascular tumors, chordomas or epidermoids.

31. The method of claim 1 wherein the compound has the structure:

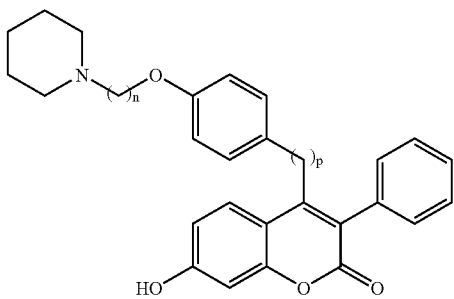

or a pharmaceutically acceptable salt thereof.

32. The method of claim 1 wherein the compound has the structure:

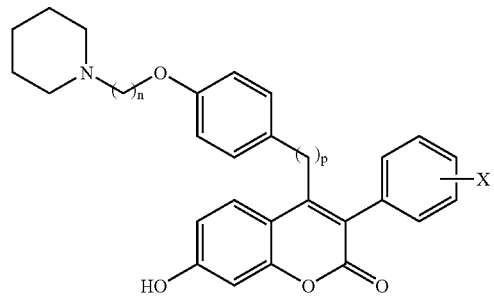

wherein X represents halogen, —OH, —R', —OR', —COOH, —COOR', —COR', —CONH$_2$, —NH$_2$, —NHR', —NR'R', —SH, —SR', —SOOR', —SOOH or —SOR', where each occurrence of R' is independently an unsubstituted or substituted $C_{1-8}$alkyl, $C_{6-12}$aryl, $C_{7-12}$aralkyl, $C_{3-12}$heterocycle or $C_{4-16}$heterocyclealkyl, or a pharmaceutically acceptable salt thereof.

33. The method of claim 32 wherein the compound has the structure:

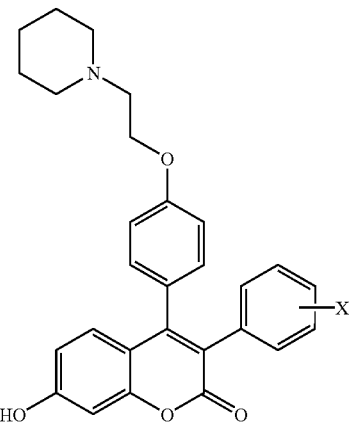

or a pharmaceutically acceptable salt thereof.

34. The method of claim 33 wherein the compound has the structure:

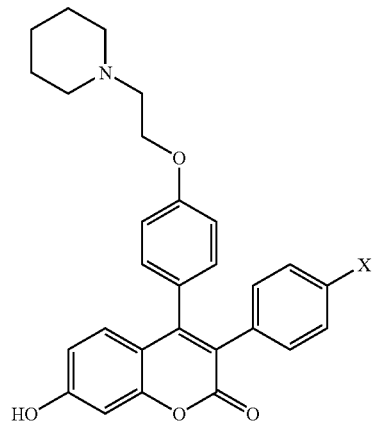

wherein X is halogen, or a pharmaceutically acceptable salt thereof.

35. The method of claim 1 wherein the compound has the structure:

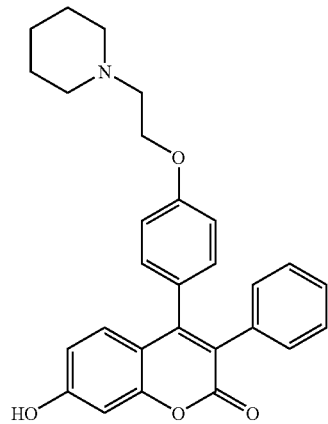

or a pharmaceutically acceptable salt thereof.

36. The method of claim 1, wherein the compound has the structure:

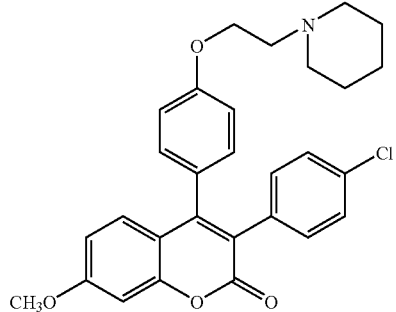

or a pharmaceutically acceptable salt thereof.

37. The method of claim 1, wherein the compound has the structure:

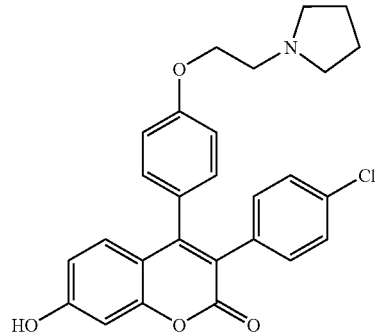

or a pharmaceutically acceptable salt thereof.

38. The method of claim 1, wherein the compound has the structure:

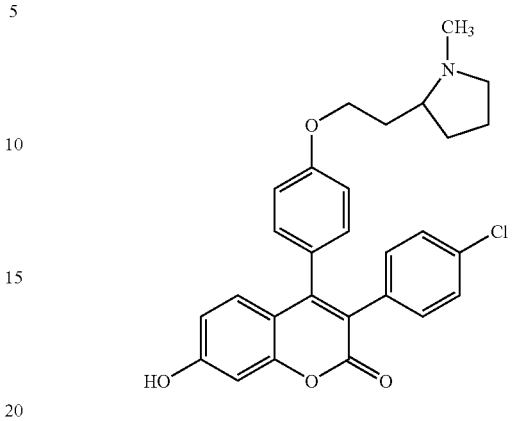

or a pharmaceutically acceptable salt thereof.

39. The method of claim 1, wherein the compound has the structure:

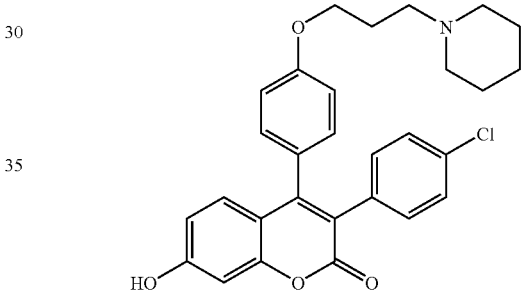

or a pharmaceutically acceptable salt thereof.

40. The method of claim 1, wherein the compound has the structure:

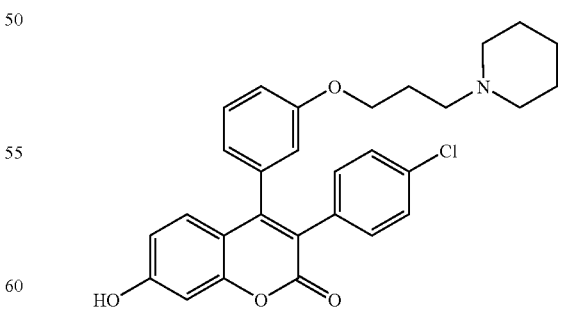

or a pharmaceutically acceptable salt thereof.

41. The method of claim 1, wherein the compound has the structure:

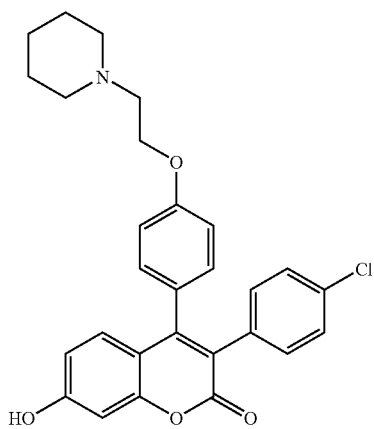

or a pharmaceutically acceptable salt thereof.

42. The method of claim 1, wherein the compound has the structure:

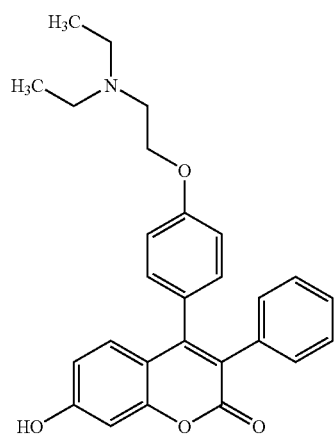

or a pharmaceutically acceptable salt thereof.

43. The method of claim 1, wherein the compound has the structure:

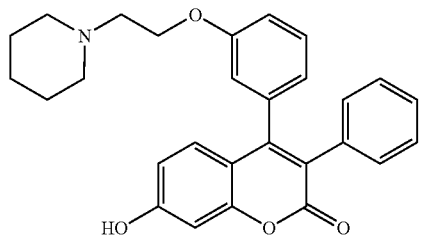

or a pharmaceutically acceptable salt thereof.

44. The method of claim 1, wherein the structure:

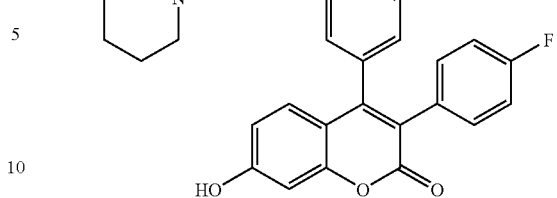

or a pharmaceutically acceptable salt thereof.

45. The method of claim 1, wherein the compound has the structure:

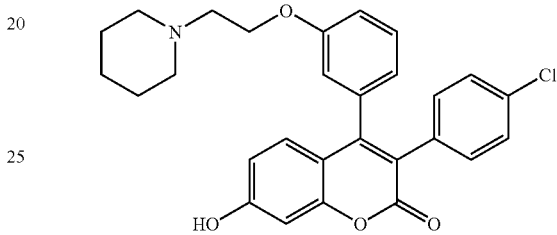

or a pharmaceutically acceptable salt thereof.

46. The method of claim 1, wherein the compound has the structure:

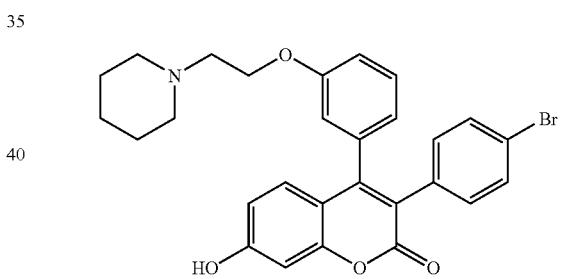

or a pharmaceutically acceptable salt thereof.

47. The method of claim 1, wherein the compound has the structure:

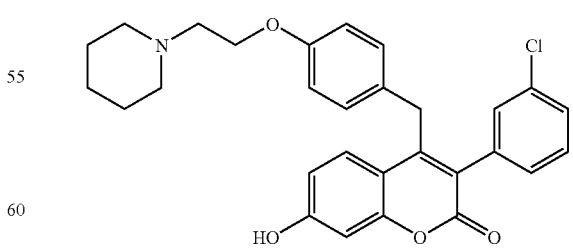

or a pharmaceutically acceptable salt thereof.

48. The method of claim 1, wherein the compound has the structure:

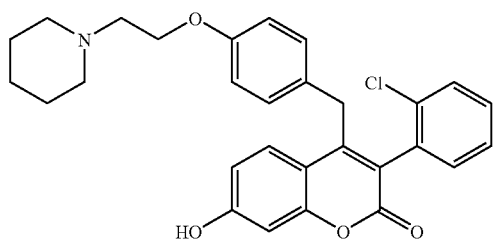

or a pharmaceutically acceptable salt thereof.

49. The method of claim 1, wherein the compound has the structure:

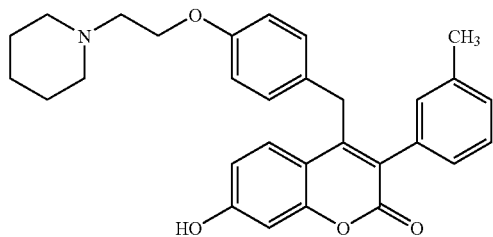

or a pharmaceutically acceptable salt thereof.

50. The method of claim 1, wherein the compound has the structure:

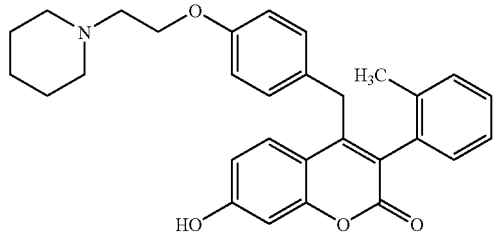

or a pharmaceutically acceptable salt thereof.

51. The method of claim 1, wherein the compound has the structure:

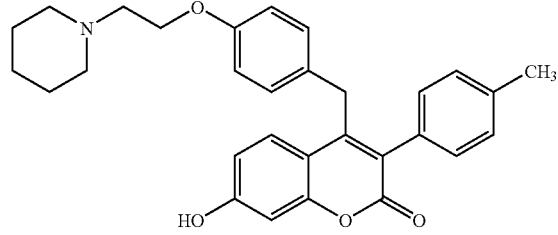

or a pharmaceutically acceptable salt thereof.

52. The method of claim 1, wherein the compound has the structure:

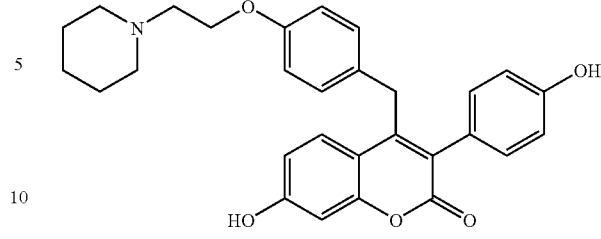

or a pharmaceutically acceptable salt thereof.

53. The method of claim 1, wherein the compound has the structure:

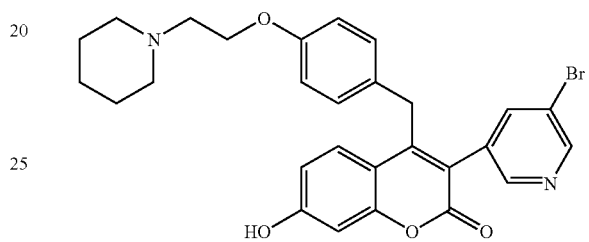

or a pharmaceutically acceptable salt thereof.

54. The method of claim 1, wherein the compound has the structure:

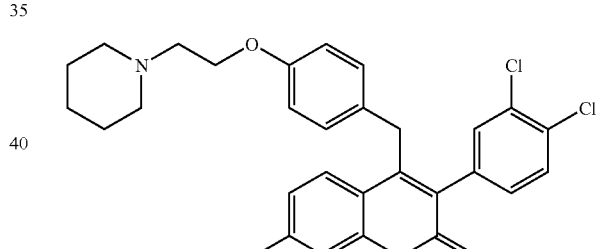

or a pharmaceutically acceptable salt thereof.

55. The method of claim 1, wherein the compound has the structure:

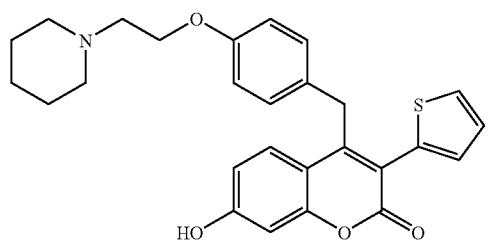

or a pharmaceutically acceptable salt thereof.

56. The method of claim 1, wherein the compound has the structure:

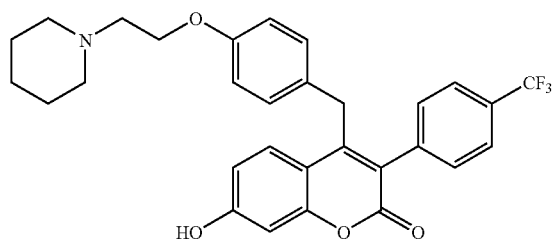

or a pharmaceutically acceptable salt thereof.

57. The method of claim 1, wherein the compound has the structure:

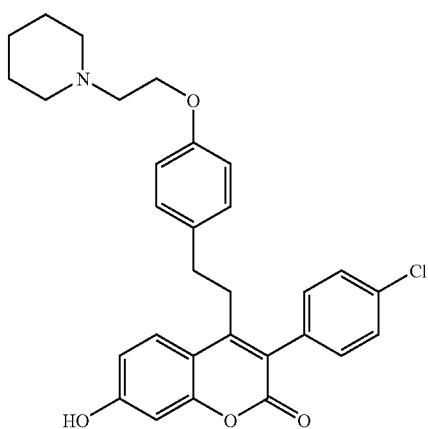

or a pharmaceutically acceptable salt thereof.

58. The method of claim 1, wherein the compound has the structure:

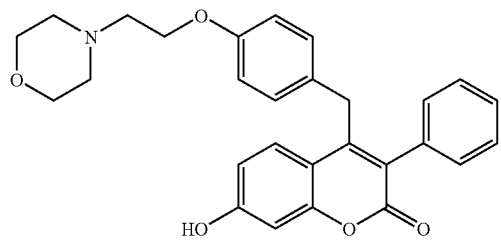

or a pharmaceutically acceptable salt thereof.

59. The method of claim 1, wherein the compound has the structure:

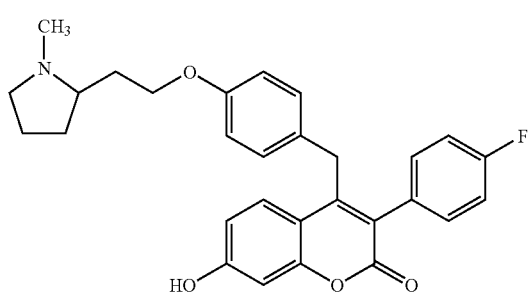

or a pharmaceutically acceptable salt thereof.

60. The method of claim 1, wherein the compound has the structure:

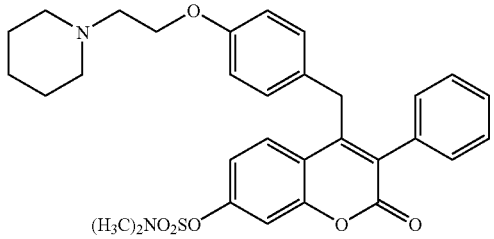

or a pharmaceutically acceptable salt thereof.

61. The method of claim 1, wherein the compound has the structure:

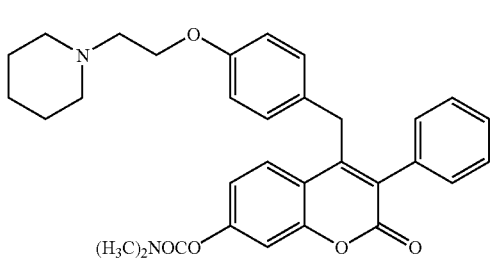

or a pharmaceutically acceptable salt thereof.

62. The method of claim 1, wherein the compound has the structure:

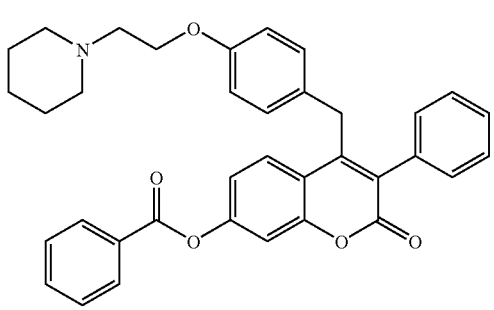

or a pharmaceutically acceptable salt thereof.

63. The method of claim 1, wherein the compound has the structure:

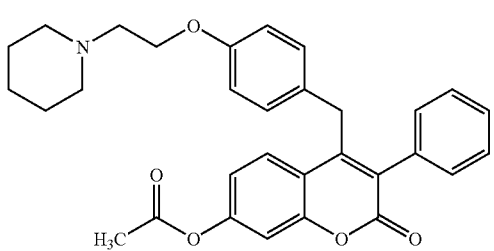

or a pharmaceutically acceptable salt thereof.

64. The method of claim 1, wherein the compound has the structure:

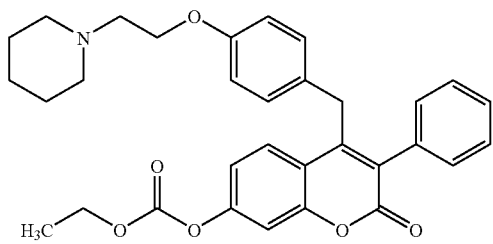

or a pharmaceutically acceptable salt thereof.

65. The method of claim 1, wherein the compound has the structure:

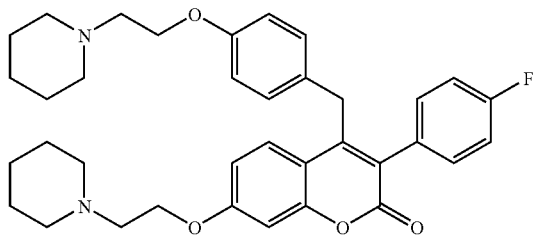

or a pharmaceutically acceptable salt thereof.

66. The method of claim 1, wherein the compound has the structure:

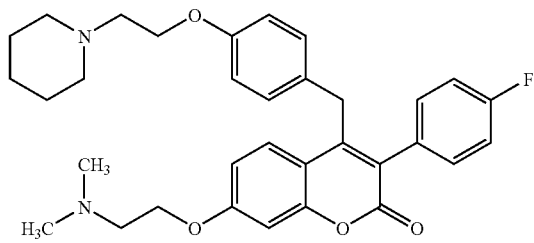

or a pharmaceutically acceptable salt thereof.

67. The method of claim 1, wherein the compound has the structure:

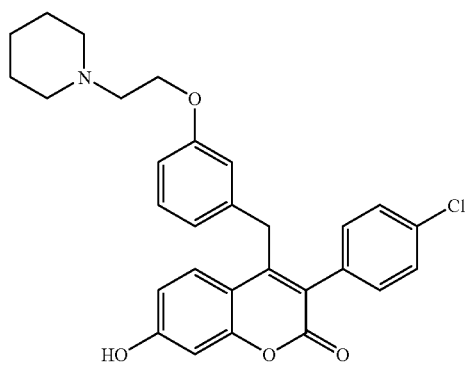

or a pharmaceutically acceptable salt thereof.

68. The method of claim 1, wherein the compound has the structure:

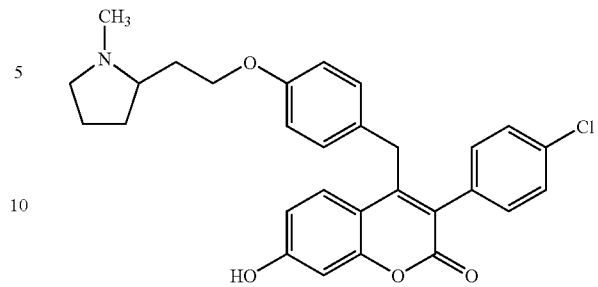

or a pharmaceutically acceptable salt thereof.

69. The method of claim 1, wherein the compound has the structure:

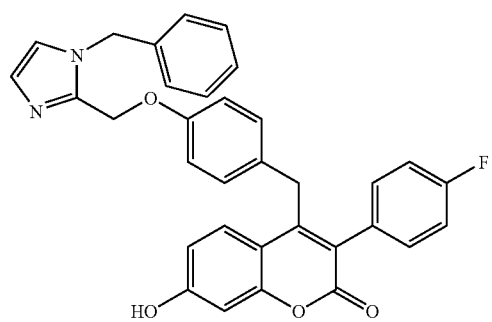

or a pharmaceutically acceptable salt thereof.

70. The method of claim 1, wherein the compound has the structure:

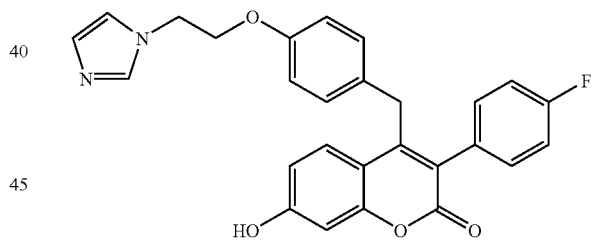

or a pharmaceutically acceptable salt thereof.

71. The method of claim 1, wherein the compound has the structure:

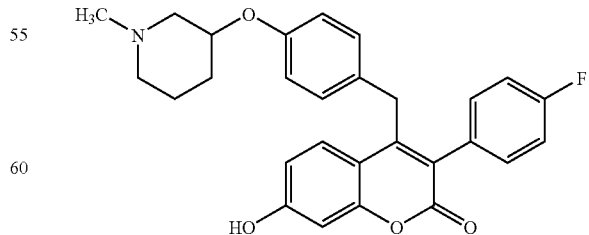

or a pharmaceutically acceptable salt thereof.

72. The method of claim 1, wherein the compound has the structure:

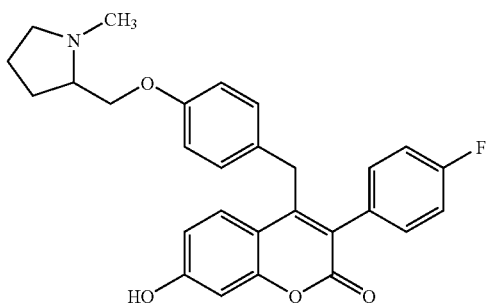

or a pharmaceutically acceptable salt thereof.

73. The method of claim 1, wherein the compound has the structure:

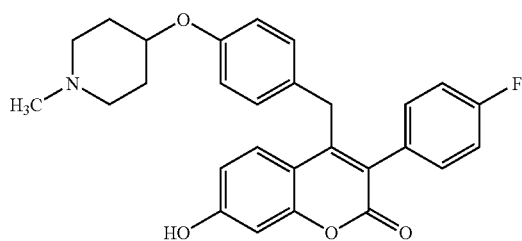

or a pharmaceutically acceptable salt thereof.

74. The method of claim 1, wherein the compound has the structure:

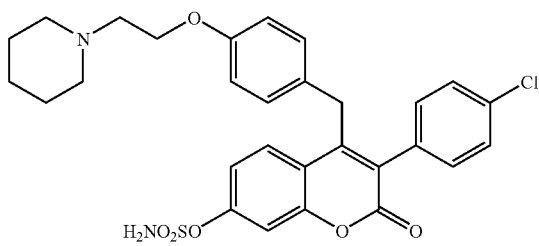

or a pharmaceutically acceptable salt thereof.

75. The method of claim 1, wherein the compound has the structure:

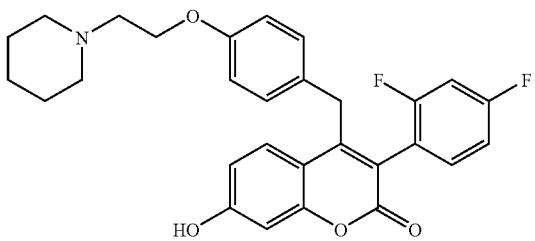

or a pharmaceutically acceptable salt thereof.

76. The method of claim 1, wherein the compound has the structure:

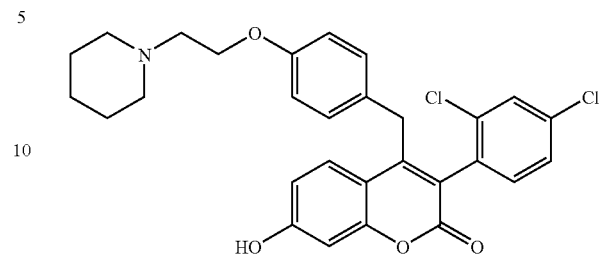

or a pharmaceutically acceptable salt thereof.

77. The method of claim 1, wherein the compound has the structure:

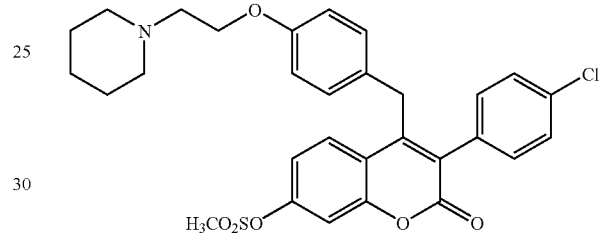

or a pharmaceutically acceptable salt thereof.

78. The method of claim 1, wherein the compound has the structure:

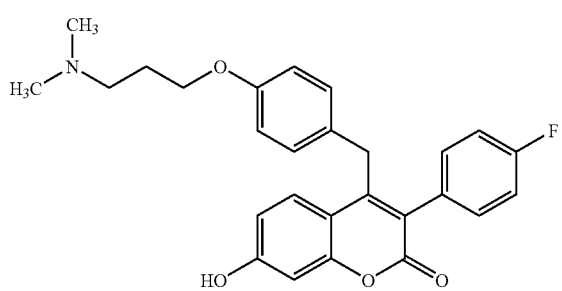

or a pharmaceutically acceptable salt thereof.

* * * * *